（12）United States Patent
Pizza et al.

(10) Patent No.: US 7,666,436 B1
(45) Date of Patent: Feb. 23, 2010

(54) PERTUSSIS TOXIN MUTANTS, BORDETELLA STRAINS CAPABLE OF PRODUCING SUCH MUTANTS AND THEIR USE IN THE DEVELOPMENT OF ANTIPERTUSSIS VACCINES

(75) Inventors: Mariagrazia Pizza, Siena (IT); Antonello Covacci, Siena (IT); Rino Rappuoli, Castelnuovo Berardenga (IT); Luciano Nencioni, Poggibonsi (IT)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 08/431,673

(22) Filed: May 2, 1995

Related U.S. Application Data

(60) Division of application No. 08/261,691, filed on Jun. 17, 1994, now Pat. No. 7,427,404, which is a continuation of application No. 07/515,563, filed on Apr. 27, 1990, now abandoned.

(30) Foreign Application Priority Data

| Apr. 28, 1989 | (IT) | .................................... 20341/89 |
| Feb. 7, 1990 | (IT) | .................................... 19286/90 |

(51) Int. Cl.
*A61K 39/10* (2006.01)
*C07K 14/235* (2006.01)
*C07H 21/04* (2006.01)

(52) U.S. Cl. .............. 424/240.1; 424/254.1; 424/185.1; 536/23.7; 530/350; 514/2; 514/12

(58) Field of Classification Search .............. 435/252.3, 435/252.1, 172.3; 424/93.2, 93.4, 240.1, 424/254.1, 185.1; 536/232, 237, 23.7; 935/10; 530/350; 514/2, 12
See application file for complete search history.

(56) References Cited

U.S. PATENT DOCUMENTS

| 4,883,761 | A | 11/1989 | Keith et al. ............. 435/252.33 |
| 5,085,862 | A | 2/1992 | Klein et al. ............. 424/197.11 |
| 5,221,618 | A | 6/1993 | Klein et al. ................. 435/69.1 |

OTHER PUBLICATIONS

Barbieri et al., "ADP-Ribosyltransferase Mutations in the Catalytic S-1 Subunit of Pertussis Toxin," Infection and Immunity, pp. 1934-1941, Aug. 1988.
Nicosia et al., "Cloning and sequencing of the pertussis toxin genes: Operon structure and gene duplication," Proc. Natl. Acad. Sci. USA, vol. 83, pp. 4631-4635, Jul. 1986.
Pizza et al., "Mutants of Pertussis Toxin Suitable for Vaccine Development," Science, vol. 246, pp. 497-500, Jul. 27, 1989.
Pizza et al., "Subunit S1 of pertussis toxin: Mapping of the regions essential for ADP-ribosyltransferase activity," Proc. Natl. Acad. Sci. USA, vol. 85, pp. 7521-7525, Oct. 1988.
Loosmore et al., "Engineering of Genetically Detoxified Pertussis Toxin Analogs for Development of a Recombinant Whooping Cough Vaccine," Infection and Immunity, pp. 3653-3662, Nov. 1990.
Podda et al., "Phase I clinical trial of an acellular pertussis vaccine composed of genetically detoxified pertussis toxin combined with FHA and 69 kDa," Vaccine, vol. 9, pp. 146-150, Oct. 1991.
Podda et al., "Acellular pertussis vaccine composed of genetically inactivated pertussis toxin: Safety and immunogenicity in 12- to 24 and 2- to 4-month-old children," Journal of Pediatrics, pp. 151-156, May 1992.
Del Giudice et al., "Priming to Heat Shock Proteins in Infants Vaccinated against Pertussis," The Journal of Immunology, vol. 150, pp. 2025-2031, No. 5, Mar. 1993.
Podda et al., "Comparative study of a whole-cell pertussis vaccine and a recombinant acellular pertussis vaccine," Journal of Pediatrics, pp. 921-926, Jun. 1994.
Zealey et al., "Construction of *Bordetella pertussis* Strains That Overproduce Genetically Inactivated Pertussis Toxin," Applied and Environmental Microbiology, pp. 208-214, Jan. 1992.

*Primary Examiner*—Chih-Min Kam
(74) *Attorney, Agent, or Firm*—Felicity E. Groth; Robert Gorman

(57) ABSTRACT

New pertussis toxin (PT) mutants are described being immunologically active and having reduced or no toxicity, characterized in that at least one of the amino acid residues Glu129, Asp11, Trp26, Arg9, Phe50, Asp1, Arg13, Tyr130, Gly86, Ile88, Tyr89, Tyr8, Gly44, Thr53 and Gly80 of subunit S1 amino acid sequence is deleted and substituted by a different amino acid residue selected in the group of natural amino acids; *Bordetella* strains capable of providing and secreting said PT mutants and means and methods for obtaining them are also described. The *Bordetella* strains and the PT mutants produced by them are particularly suitable for the preparation of effective cellular and acellular antipertussis vaccines.

9 Claims, 8 Drawing Sheets

FIGURE 9

WILD-TYPE PERTUSSIS TOXIN S1 SUBUNIT

PERTUSSIS TOXIN MUTANTS, BORDETELLA STRAINS CAPABLE OF PRODUCING SUCH MUTANTS AND THEIR USE IN THE DEVELOPMENT OF ANTIPERTUSSIS VACCINES

This is a division of application Ser. No. 08/261,691, filed Jun. 17, 1994, now U.S. Pat. No. 7,427,404, which is a continuation of Ser. No. 07/515,563, filed Apr. 27, 1990, now abandoned. Applicants claim priority benefit under 35 USC § 120 of their copending application Ser. No. 08/261,668, filed Jun. 17, 1994, now U.S. Pat. No. 6,713,072, which is a continuation of Ser. No. 07/265,742, filed Nov. 1, 1988, now abandoned.

The present invention refers to new, immunologically active pertussis toxin strains having reduced or no toxicity, capable of producing and secreting mutated pertussis toxin proteins, means and methods for their preparation, and their use for developing effective antipertussis vaccines.

The present invention also refers to immunogenic formulations suitable as antipertussis vaccines containing as an active principle at least one immunogenically active pertussis toxin mutant and having reduced or no toxicity, which may have been treated with formaldehyde, or a *Bordetella* strain capable of producing and secreting said mutant, or a Δ tox *Bordetella* strain incapable of producing the pertussis toxin.

Pertussis, an infectious disease of bacterial origin characterized by accesses of convulsive cough and serious respiratory sinthomatology, affects individuals of all ages and, in the first years of life, is lethal in 0.5% of cases.

*Bordetella pertussis* (*B. pertussis*), which is the etiological agent of pertussis, produces during the virulent stage (stage I) a series of toxic components among which the pertussis toxin (PT) represents not only the principal pathogenic agent of the disease but also the major immunogen.

PT, which has the structure of a hexamer consisting of five different subunits (S1, S2, S3, S4, and S5, in the ratio of 1:1:1:2:1) is capable in fact of inducing in experimental animals antibody levels sufficient to impart a protection against pertussis.

The incidence of the infection may be controlled by immunization of an individual with a suitable vaccine. At present a cellular vaccine is employed, that is a vaccine consisting of whole cells of virulent *B. pertussis* treated with merthiolate and killed at 56° C. Said vaccine, although imparting a protective immunity, may produce, however, undesirable side effects ranging from simple pomphuses, erythema and fever to convulsions and cerebral damages. For these reasons, the use of said vaccine has been drastically reduced in the last few years, resulting in a new outbreak of the disease.

Acellular vaccine were therefore proposed in the technique consisting of one or more antigen, toxic proteins produced and secreted by virulent *B. pertussis*, detoxified with a variety of chemicals reagents such as formaldehyde (Sato et al. (1983), Infect. Immun., 41, 313-320), glutaraldehyde (Quentin-Millet et al. (1988) J. Bio. Stand., 16, 99-108), tetranitromethane (Siber et al. 1988; Windberry et al., 1988, International Workshop of *Bordetella pertussis*, Hamilton, Mo.), trinitrobenzensulfonic acid (Fisch et al., 1984, Infect. Immun, 44, 1-16), hydrogen peroxide (Sekura et al., (1983), Infect. Immun., 113:806-813).

Said detoxification methods present, however, the following drawbacks:
  reversion of protein toxicity. In fact, acellular vaccines consisting only of formaldehyde detoxified PT or of PT and filamentous hemagglutinin (FHA)) both treated with formaldehyde (Sato Y. et al. (Lancet 1, 122-126, 1984), although being capable of protecting 80% of the children from the disease and 50 to 60% from the infection (Ad hoc Group for the Study of Pertussis Vaccines, 1988, Lancet 1, 959-960), show a reversion of the toxicity (Sortsaeter J. et al., Pediatr. Infect. Dis. J., 7, 637-645. 1988).
  reduced immunogenicity of the antigen proteins caused by the drastic conditions required in the detoxification stage;
  absence of reproducibility of the detoxified products;
  necessity of tests to evaluate the reversion for each preparation, tests which requires a long time, and finally
  risks in handling large amounts of toxic material for the people employed in the preparation of such antigen proteins.

As known, the toxicity of the pertussis toxin is mediated by the ADP-ribosyl-transferase activity of its S1 subunit. To the end of obtaining molecules with an altered toxicity with respect to the wild type pertussis toxin (PT), suitable for the preparation of pertussis vaccines free of the above mentioned drawbacks, a series of deletion mutants of the N-terminal and/or C-terminal portion of S1 were constructed and expressed in *Escherichia coli* (*E. coli*), as well as a series of peptides, analogous to S1, containing in their sequence one or more amino acid substitutions, as disclosed in the Italian patent application No. 22481 A/87 of Nov. 2, 1987, which incorporates the disclosure of Italian patent application No. 19208-A/86 for the cloning, sequencing and expression of the genes which code for the amino acids of the S1, S2, S3, S4 and S5 subunits of pertussis toxin. The entire disclosure of the 19208/A86 application appears in its U.S. counterpart application Ser. No. 07/006,438, filed Jan. 23, 1986.

In practice, the DNA fragment encoding sub-unit S1 of the pertussis toxin was modified by site-specific mutagenesis to encode a subunit containing, in specific-sites, an amino acid residue different from the one normally present in PT. The peptides obtained through culture of said engineered *E. coli* strains showed an altered toxicity compared to the wild-type pertussis toxin. Said peptides, however, were expressed as proteins fused to an amino-terminal sequence of 98 amino acids of MS2 bacteriophage polymerase.

Furthermore, when tested in vivo (mice) said peptides were incapable of inducing the formation of protective antipertussis antibodies, probably for the reason that as such they could not show the same conformational structure that they assume in the native molecule. Therefore, processes employing host microorganism such as *E. coli* engineered by means of recombinant DNA techniques to obtain heterologous proteins (that is, proteins that are not naturally produced by said host strains) do not appear suitable for the preparation of products having the desired immunogenic properties.

An objective of the present invention is to obtain immunogens suitable for the preparation of antipertussis vaccines devoid of the setbacks of the prior technique. This is obtained according to the present invention by providing new *Bordetella* strains capable of expressing and secreting pertussis toxin mutants with reduced or no toxicity.

An object of the present invention is therefore obtaining immunogenically active mutants having reduced or no toxicity, characterized by containing in specific sites of the subunit S1 sequence one or more deleted amino acid residues or amino acid residues substituted by a different amino acid residue.

A further objective of the present invention is an immunogenically active pertussis toxin mutant protein, free of toxicity or having a reduced toxicity, characterized by thermal stability and by reduced or absent mitogenenetic and hemagglutination properties, obtained by treatment with wt/vol percentage of formaldehyde of between 0.035% and 0.420%.

Still further objectives of the present invention are *Bordetella* strains capable of producing and secreting immunogenically active pertussis toxin mutant proteins presenting a reduced or no toxicity. Another objective of the present invention is a method for preparing such *Bordetella* strains.

Still another object of the present invention is a process for the preparation of immunogenically active pertussis toxin mutant proteins with reduced or no toxicity, which comprises cultivating in suitable conditions such mutated *Bordetella* strains.

A further objective of the present invention is the use of *Bordetella* strains capable of producing and secreting immunogenically active mutants of the pertussis toxin showing reduced or no toxicity, and/or Δ tox *Bordetella* strains incapable of producing pertussis toxin, for the preparation of effective antipertussis cellular vaccines.

A further objective of the present invention is the use of immunogenically active mutant pertussis toxins with reduced or no toxicity possibly treated with formaldehyde for the preparation of effective antipertussis acellular vaccines.

The present invention has furthermore as an object immunogenic formulations suitable as antipertussis vaccines capable of inducing in humans an effective protective response against infections deriving from virulent *B. pertussis*. containing an immunogenically effective amount of a *Bordetella* strain as above defined.

Still further objects of the present invention are immunogenic formulations suitable as antipertussis vaccines capable of producing in humans an effective protective response against infections deriving from virulent *Bordetella pertussis*, containing an immunogenically effective amount of an immunogenically active pertussis toxin mutant having reduced or no toxicity, said mutant being possibly treated with formaldehyde.

Further objectives of the present invention will be evidenced by reading the description and examples that follow. In particular, immunogenically active mutantpertussis toxins having reduced or no toxicity according to the present invention are characterized by the fact that at least one of the amino acid residues Glu129, Asp11, Trp26, Arg9, Phe5O, Asp1, Arg13, Tyr13O, Gly86, Ile 88, Tyr89, Tyr8, Gly44, Thr53 and Gly80 of the amino acid sequence subunit of the S1 is deleted or substituted by a different amino acid residue selected from the group of standard amino acids.

Preferred pertussis toxin mutants according to the present invention are the ones characterized by the fact that amino acid residue Glu129 and at least one of the amino acid residues Arg9, Asp11, Asp13 and Trp26 are deleted or substituted by a different amino acid residue selected from the group of standard amino acids.

According to an embodiment of the present invention the pertussis toxin mutants contain the amino acids substitutions reported in Table II, column 1 where:

in the first line the name of the mutated protein is reported;
in the second line the type of mutation performed, and
in the third line the nucleotide sequence utilized for the mutation.

Particularly preferred among these are the pertussis toxin mutants designated as follows: PT28G (PT-129G), L9/28G (PT-9K/129G), L13/28G (PT-13L/129G), 126/28G (PT-26I/129G), L13/126/28G (PT-13L/26I/129G), PT-88E/89S and E88/S89/280 (PT-88E/89S/129G).

PT mutants having the above listed characteristics are obtained, according to the present invention, by cultivation of *Bordetella* strains containing the chromosomal gene encoding the PT isolated from *B. pertussis* mutagenized by site-specific mutagenesis or by deletion of nucleotides in one or more specific sites of the nucleotide sequence encoding the S1 subunit.

According to the present invention said *Bordetella* strains are obtained with the aid of a process comprising:
a) selection of wild-type *Bordetella* strains resistant to at least one antibiotic;
b) substitution through homologous recombination in the strains obtained in a) the chromosomal gene encoding pertussis toxin with a gene encoding a different protein;
c) selection of *Bordetella* strains devoid of the PT tox) gene obtained in b);
d) mutagenesis of the pertussis toxin gene isolated from *B. pertussis;*
e) introduction of the mutagenized gene into a suitably modified plasmid non-replicable in *Bordetella;*
f) introduction by conjugation of said plasmid into the *Bordetella* (Δ tox) strains selected in c), and finally
g) isolation of *Bordetella* strains in which an homologous recombination has taken place with the mutagenized pertussis toxin gene.

*Bordetella* wild type strains according to the present invention are selected among the species *B. pertussis, B. parapertussis* and *B. bronchiseptica*. The last two, although possessing the pertussis toxin operon, do not normally produce the toxin because of the absence from the operon of a functional promoter.

In stage a) of the process of the present invention, *Bordetella* strains are made resistant to one or more antibiotics in order to facilitate the selection of the mutated strains. According to an embodiment of the present invention, said *Bordetella* strains are made resistant to nalidixic acid (nal) and to streptomycin (str).

In stage b) of the process according to the present invention the substitution is performed, by homologous recombination, of the chromosomal gene encoding the PT contained in the strains obtained as in a), with a gene encoding for a protein different from PT, for instance a Kanamycin resistance gene (kan). The recombination may be performed, employing generally known techniques, employing a plasmid non replicable in *Bordetella*. Preferably plasmid pRTP1, which was described by Stibitz S. et al (GENE, 50, 133-140, 1986), is employed the construction.

Said plasmid may be introduced into the *Bordetella* cells by conjugation of two components using a *E. coli* strain, or at three components using a *E. coli* strain containing a so called helper plasmid. According to the present invention the pRTP1 plasmid is digested with the EcoRI restriction enzyme and then ligated with a DNA EcoRI fragment containing the gene that encodes for a protein different from PT and comprised among the nucleotide sequences corresponding to regions 1-420 and 3625-4696 of the *B. pertussis* PT gene contained in the PT101 ATCC 67854 plasmid. *E. coli* cells are then transformed with the resulting plasmid, and the transformants are selected employing conventional techniques.

The thus selected positive clones are then conjugated with the *Bordetella* strains obtained in a), previously cultivated on BordetGengou (BG) medium at 37° C. for about 48 hours. The conjugation is performed, according to conventional techniques, in BG medium with added 10 mM MgCl2 at 37° C. for 3-6 hours.

In stage c) of the process according to the present invention the *Bordetella* strains, in which a homologous recombination at the chromosomal level has taken place, are selected on GB medium made selective by the addition of suitable antibiotics.

When nal and str resistant *Bordetella* strains are employed and the gene different from PT is the one of Kanamycin resistance, the antibiotics added to the medium are nal, str and kan.

The strains that grow on this medium (resistant to the three antibiotics) are the ones in which the complete substitution of the PT gene by the Kanamycin resistance gene has taken place and which have lost the pRTP1 plasmid which imparts sensitivity to streptomycin.

For the purpose of confirming such substitution, said strains indicated in what follows as Δ tox, were characterized by means of Southern blot (E. Southern, J. Mol; Biol; (1975) 9-8. 503-517), ELISA assay (Wong, K. H. and Skelton S. K. J., Clinical Microbiol. Vol. 26, 1316-1320, 1988) and toxicity test on CHO cells (Hewlett, E. L. et al (1983) Infect. Immun. 40. 1198-1230). The results have shown:

a) the chromosomal DNA presence in the Δ tox strains of a nucleotide fragment with a molecular weight lower than that of the DNA fragment encoding the PT gene, which hybridizes both with the PT gene and with the gene used to create the conjugate (Kanamycin resistance gene);

b) none of the Δ tox strains is capable of producing and secreting pertussis toxin in an amount detectable by ELISA assay;

c) the toxicity on CHO cells, determined employing the supernatant of *Bordetella* Δ tox cultures diluted 1/10 does not modify growth of the CHO cells. A slight, non-specific toxicity is observed employing the supernatant as such.

For the purpose of ascertaining the capacity of said Δ tox strains of imparting a protection against virulent *B. pertussis*, a "intracerebral challenge" assay is performed as described in "21/PAR7620.4 CODE OF FEDERAL REGULATIONS, Potency test of pertussis vaccine". The obtained results, reported in Example 1, show that said strains, although no longer possessing the PT encoding gene, are still capable of inducing an excellent protection against intracerebral infections due to virulent *B. pertussis*.

In stage d) of the process of the present invention the construction of the mutagenized PT gene is performed by deletion or substitution through site-specific mutagenesis, of one or more nucleotides in determined positions of the nucleotide sequence of the gene which encodes for the S1 subunit of the *B. pertussis* PT contained in the PT101 ATCC 67854 plasmid.

According to one embodiment of the present invention, PT genes are constructed containing the mutations reported in Table II, utilizing the nucleotide sequences listed in line 3 of the first column.

In stage e) of the process of the present invention, the mutagenized genes obtained in stage d) are cloned in a plasmid non-replicable in *Bordetella*. To that end, plasmid pRTP1 is utilized, modifying it by insertion in its BamHI restriction site the gene encoding resistance to gentamycin or the one encoding for resistance to tetracycline, both commercially available. Cloning such genes is performed according to one of the known techniques generally employed in genetic engineering. The new vectors, indicated respectively as pRTPG1 and pRTPT1 are thus employed to insert the mutagenized PT gene into the chromosome in the *Bordetella* Δ tox strains.

In particular, the mutagenized genes are cloned in plasmids pRTPG1 and pRTPT1 and the resulting recombinant plasmids are introduced, by transformation in *E. coli* cells. The transformants are conjugated with, Δ tox *Bordetella* strains as described above. *E. coli* cells suitable for the purposes of the present invention are *E. coli* SM10 described by Simon R. et al Biotech. 1. 784-791, 1983. Finally, in stage g) of the process of the present invention the selection of *Bordetella* strains containing in their chromosome the mutagenized PT gene is performed.

In particular, first the selection of *Bordetella* strains is performed which contain the recombinant plasmid integrated in the chromosome, by cultivating on BG medium with added nal and gentamicin or nal and tetracycline. Then selection of strains which have lost said plasmid, by cultivation on BG medium containing str is performed. Finally, the colonies capable of growing on this medium are isolated and cultivated on BG medium containing nal, str and kan or nal and str. operating in this way on this last medium, *Bordetella* colonies are selected which have lost the kanamycin resistance phenotype because of the substitution of kan gene with the mutagenized PT gene.

In order to ascertain the capacity of said *Bordetella* strains to express and secrete the PT mutants encoded by the mutagenized chromosomal gene, some of these strains are cultivated in a suitable medium, such as for instance the medium having the composition reported in Example 1. The production data show:

the *B. pertussis* strains produce the PT mutants in amounts comparable to the ones obtained by cultivating the same wild type strains;

the *B. bronchiseptica* and *B. parapertussis* strains which do not normally produce the PT toxin, are surprisingly capable of producing and secreting it in the culture medium, and the *B. parapertussis* strain produces it in higher amounts than the *B. pertussis*.

Said results show that the substitution of the inactive promoter, present in said wild type *Bordetella*, by an efficient promoter such as, for example, the one of the *B. pertussis* PT, allows the expression in said strains and of PT or of mutants of PT.

According to the present invention the PT mutants obtained as said are purified from the acellular medium utilizing purification techniques selected among the ones known to the expert in the field, e.g., such as the one described by Sekura R. D. et al, J. Biol. Chem. 258. 14647-14651 (1983).

According to the present invention, the physico-chemical, biological and immunological properties of certain PT mutants were determined in vitro and in vivo. As far as the physico-chemical properties are concerned, the analysis by electrophoresis in SDS on polyacrylamide gel (SDS-PAGE) shows the absence of contaminant proteins and a pattern identical to the one of PT, while the amino acid analysis shows an amino acid composition in agreement with the values predicted on the basis of the known amino acid sequence.

Furthermore, the absence of dimethyl (2,6-0-) beta-cyclodextrin is confirmed employing the method described by Beley J. G. (1985), "Laboratory techniques in biochemistry and molecular biology", Burdon R. H. and Van Knippennberg P. H. (edit.) Elsevier vol. 16, the absence of fetuin, of protein 69 KD and of filamentous hemagglutinin, which are the possible contaminants of acellular antipertussis vaccines, by means of Western Blotting analysis (Towbin H. T. et al (1976). P.N.A.S., USA. 73, 361-365) utilizing antibodies specific for such proteins. Finally, the absence of dermonecrotic toxin is confirmed by means of the assay performed on guinea pigs as described by Kime K. T. et al., (1986), (Infect. Immun., 52. 370-377), while the absence of cyclodextrin which is a prevalent component of the culture medium, is proved by thin layer chromatography. The absence or reduction of the PT mutants according to the toxicity of the present invention is determined in various experimental systems in vitro and in vivo.

The results obtained in the CHO (Chinese Hamster Ovary Cells) cells assay show a reduction down to disappearance of the toxicity, compared to the native PT, of from 10 to 1,000,000 times. In particular, the best results are obtained using the PT-129G, PT9K/129G, PT-13L/129G, PT-26I/129G, PT-13L/26I/129G, PT-88E/89S and PT88E/89S/129G mutants.

Furthermore, in none of the other assays was any toxicity of the product observed at the maximum employed doses. Such results confirm that all the toxic PT activities are due to the ADP-ribosyltransferase activity of its S1 subunit.

The only activities of the mutant PT which are not altered by the genetic manipulations of the S1 subunit are the mitogenicity VS cells and the hemagglutinating capacity, which, as known, are imparted to the molecule by the presence of the B oligomer.

In fact Bordetella strains according to the present invention which secrete only said oligomer (indicated with B in Table II) assayed in vitro for the presence of mitogenetic activity confirm said teachings of the known technique. Although the role of said in vivo activity is still nuclear, one can foresee that it should be minimal or absent, because in order to have in vitro an ascertainable mitogenic effect, high concentrations (0.3-1.0 µg/ml) are necessary. Such concentrations are only present in the site of vaccine inoculation.

According to the present invention, while, however, not limiting it, the immunogenic properties of the PT-9K/129G mutant are tested in vivo as reported in the examples that follow. The results show that said mutant is capable of inducing the formation of anti-PT antibodies with a high antibody titer and that said antibodies are capable of neutralizing the PT toxic effect on CHO cells.

One can therefore conclude that the genetic manipulations performed for the construction of the mutagenized PT gene do not alter the typical immunogenic properties of the pertussis toxin and that, differently from what reported in the known technique, said properties are independent from the enzymatic activity of the PT S1 subunit.

The Bordetella strains and the enzymatically inactive PT mutants (with reduced or no toxicity) obtained according to the present invention, are therefore excellent candidates for the development of effective pertussis vaccines.

In accordance with the present invention, immunogenic formulations suitable as antipertussis vaccines may be prepared by adding said strains or the mutant PT proteins produced by them to a pharmaceutically acceptable carrier selected among the ones generally used as vehicles for immunogenic materials in a patient. An example of such carriers is saline solution. The antigen product may be present in the carrier in solution or in suspension. Said formulations may also comprise an adjuvant to stimulate the immunity response and therefore improve the vaccine effectiveness. Suitable adjuvants, to the ends of the present invention, include, for instance, aluminium phosphate, aluminium hydroxide, interleukin-1 or interleukin-2 or their peptide fragments.

Immunogenic formulations suitable as antipertussis vaccines contain, generally, a final concentration of strains and of mutant toxins produced by them selected in order to impart an effective immunity against pertussis. The vaccine, after formulation, may be introduced into a sterile container and kept at various temperatures, for instance 4°, 20° or 37° C. or lyophilized. To induce an effective immunity against pertussis, one or more doses of the conveniently formulated vaccine may be administered. Vaccines according to the present invention may be administered according to conventional methods. The treatment may consist in administering one dose or successive doses. Vaccines according to the present invention may comprise one or more antigen components such as, for example, tetanus toxoid or diphtheria toxoid or other Bordetella antigens.

In order to assure the best formulations to be included in a antipertussis vaccine, PT mutants may be stabilized with formaldehyde in amounts, expressed in wt/vol, of between 0.035% and 0.420%. corresponding, that is, to a PT mutant/formaldehyde wt. ratio of between 0.300 and 0.025. Formaldehyde, employed in such concentrations, beside allowing the mutant stabilization, induces a reduction and/or disappearance of mitogenicity and of the hemagglutinating activity, depending on the employed concentration, without altering the immunologic properties.

Differently from what is described in the literature for the CRM197 of diphtheria toxin, in which the formaldehyde treatment of the molecule was necessary to obtain a protective immunity, we have surprisingly found that the PT mutants, both stabilized and non stabilized with formaldehyde, show identical immunologic activities (induction of neutralizing antibodies and protection against intracerebral infections by virulent B. pertussis).

Both formulations (containing or not containing the stabilized mutant) show the same stability when kept at 20° C. or 4° C., while at 37° C. a higher stability is observed for the formaldehyde treated mutant.

Antipertussis vaccines according to the present invention show considerable advantages with respect to the ones of the known technique containing as an active principle PT detoxified by means of chemical reagents. The PT mutants obtained by genetic manipulation according to the present invention show in fact an irreversible toxicity alteration and a unaltered immunogenicity. The safety of the PT mutants according to the present invention is further confirmed by the evidence that the in viva treatment (mice and rats) with 1500 pg/kg body weight, which is 1000 times the foreseen human dose, does not lead to any local or systemic toxic reaction.

In conclusion, Bordetella strains mutated according to the present invention, and, preferably, the mutated PT toxins produced by them, are, for their high immunogenicity and absence of toxicity, particularly suitable antigens for the development of synthetic cellular and acellular antipertussis vaccines having the desired characteristics.

In accordance with the present invention, Bordetella pertussis (W28) PTL9/28G (PT-9K/1290), Bordetella parapertussis PT280 (PT-129G) and Bordetella parapertussis PTI26/28G (PT-26I/129C) were deposited at the American Type Culture Center on Apr. 5, 1989, as ATCC 53894, ATCC 53892 and ATCC 53893.

BRIEF DESCRIPTION OF THE DRAWINGS

Figure 9:
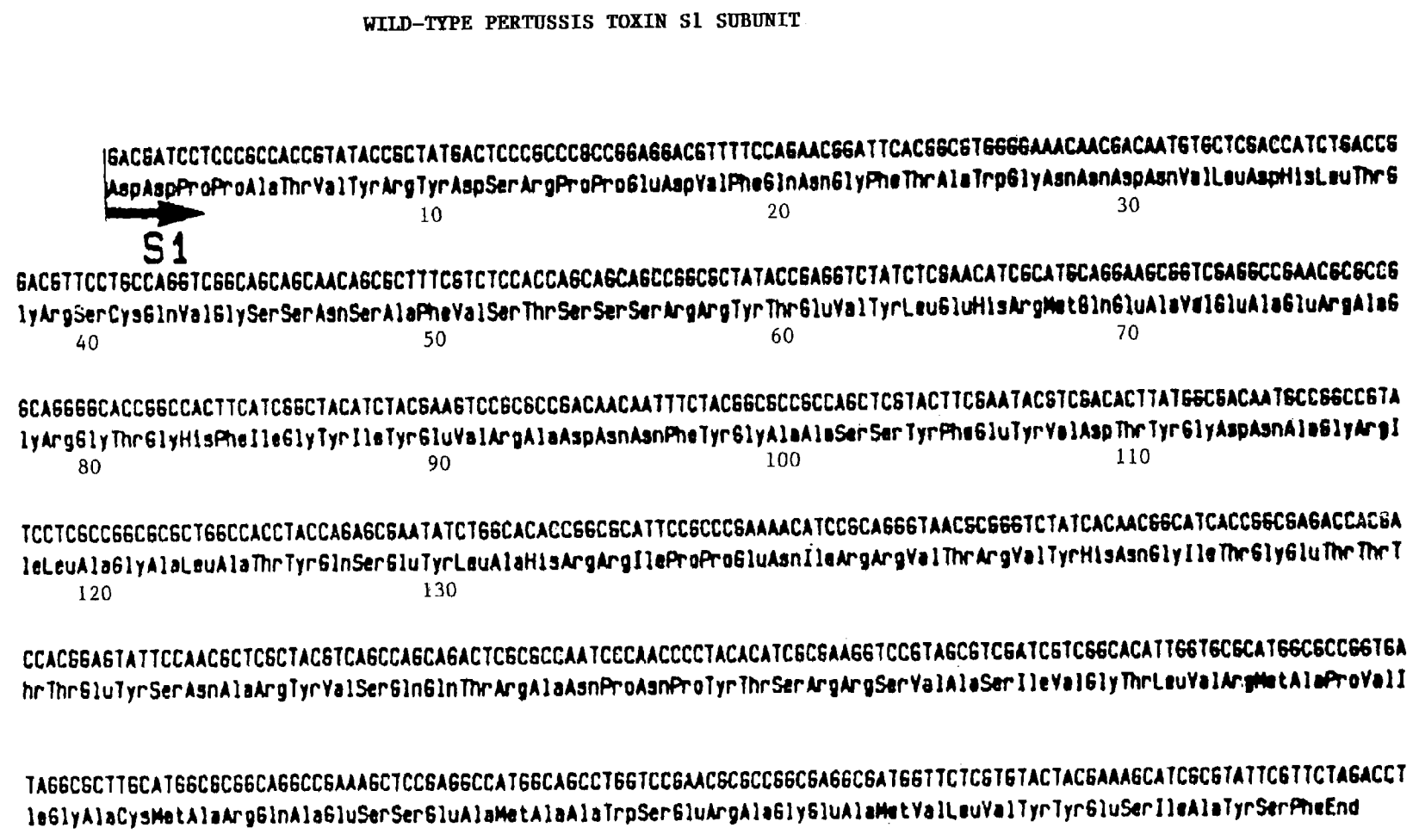

FIG. 9: This figure sets forth the amino acid sequence of the wild-type pertussis toxin S1 subunit and its corresponding DNA sequence taken from FIG. 3A.1 of Italian application Serial No. 19208-A/86, filed Jan. 28, 1986.

The following examples are illustrative and not limitative of the invention.

EXAMPLE 1

Construction of *Bordetella* (Δ tox) Mutants Free of the Pertussis Toxin Gene

*Bordetella pertussis* strains BP165, BP Tohama and BPW28 (SCLAVO S.p.A.), the one of *Bordetella parapertussis* BP14 (SCLAVO S.p.A.) and *Bordetella bronchiseptica* BP7865 (SCLAVO S.p.A.) are made resistant to streptomycin (str) and to nalidixic acid (nal).

Figure 1:
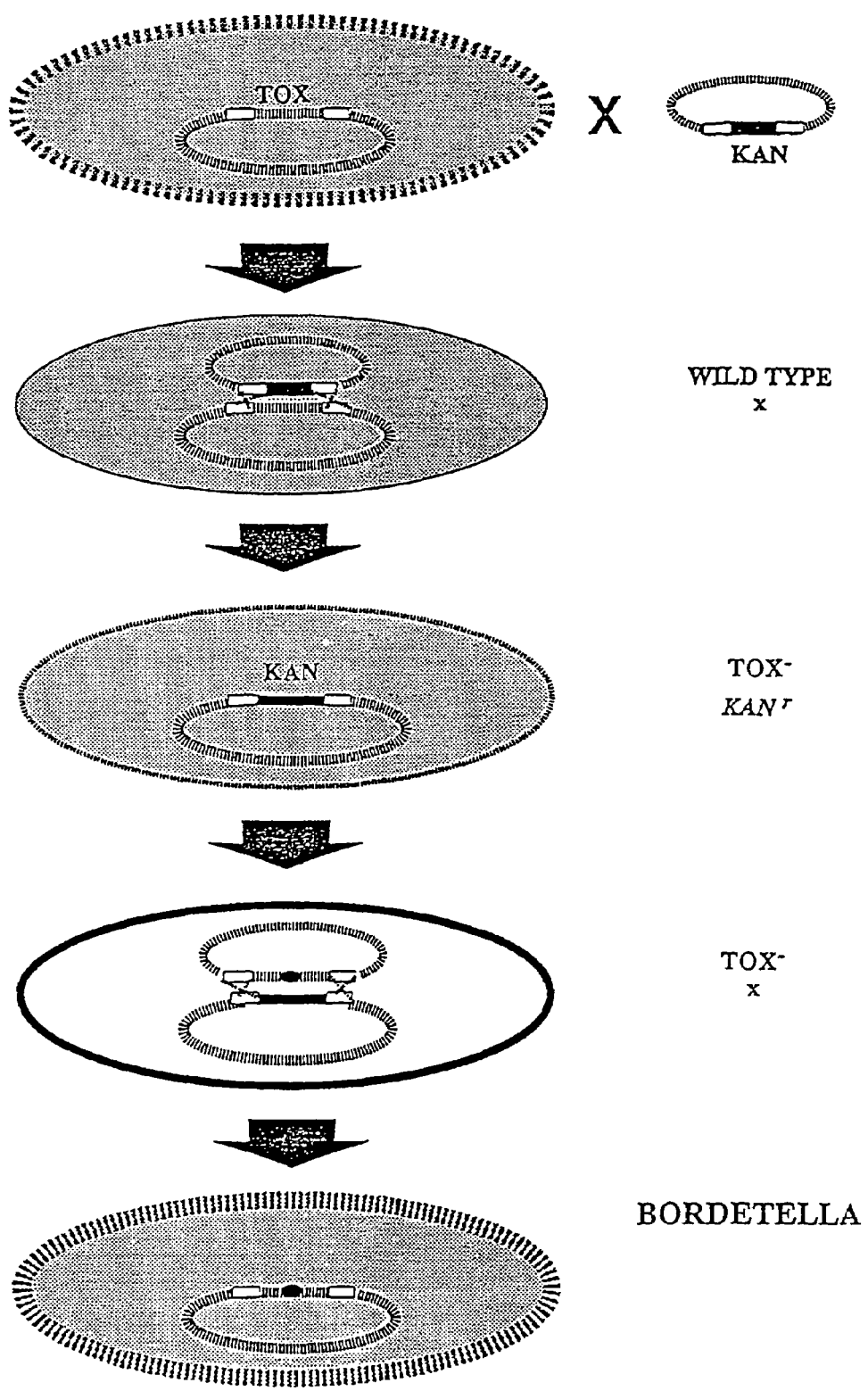
FIG. 1: schematic representation of the method employed for removing the pertussis toxin gene from the Bordetella strains chromosome and substitution with genes encoding mutated toxins or Kanamycin resistance.

In practice approximately 10$^{10}$ bacteria of each strain are plated on Bordet-Gengou (BG) agar (DIFCO) medium supplemented with 15% defibrinated sterile blood containing 800 µg/ml srt or 200 µg/ml nal and cultivated at 37° C. for about 100 hours. The spontaneous mutants grown on said plates are isolated and the gene encoding the pertussis toxin, contained in their chromosome is substituted with the Kanamycin resistance structural gene, operating according to the scheme reported in FIG. 1.

To this purpose plasmid pRTP1 (Stibitz et al. Gene, vol. 50 1986, p. 133-140) is employed which does not replicate in *Bordetella*, but can be introduced in it by conjugation. In practice, plasmid pRTP1 (10 µg) is digested with 50 units of restriction enzyme EcoRI (BRL) according to the method suggested by the supplying firm. The plasmid DNA is then ligated in 10 µl of a mixture of ligase (66 mM Tris-HCl pH 7.6. 1 mM ATP. 10 mM MgCl$_2$, 15 mM dithiothreitol) in the presence of 1 unit T4 DNA ligase, at 14° C. for one night, with 0.2 pg DNA EcoRI fragment containing the structural gene encoding resistance to Kanamycin (kan) (Pharmacia, Uppsala) comprised among the nucleotide sequences corresponding to regions 1-420 and 3626-4692 which flank the pertussis toxin structural gene. Said fragment is obtained by first digesting plasmid DNA PT101 ATCC67854 with restriction enzyme BstEII, which cuts in the only restriction sites in position 421 and 3625 and eliminating sequence 421-3625, and making then blunt-end sites BstEII by means of the Klenow enzyme. Finally, fragment HincII containing the Kan gene is ligated with the linearized plasmid DNA as reported supra in a ligase mixture in the presence of T4 DNA ligase. After approximately 18 hours at 14° C., the ligase mixture is employed to transform competent *E. coli* cells and the transformants are selected on LB agar medium with added 50 µg/ml ampicillin and 50 µg/ml Kanamycin at 35° C. for one night. Finally, from one of the positive clones the plasmid having the expected characteristics is isolated and successively digested with EcoRI restriction enzyme. The DNA fragment containing the Kanamycin resistance gene is isolated on agarose gel as described by Maniatis et al. (1983) "Methods in Enzymology".

Said EcoRI fragment is then ligated with pRTP1 plasmid previously digested with EcoRI and the resulting ligase mixture is employed to transform *E. coli* SM10 cells described by Simon R. et al. (Biotechnol., vol. 1. pp. 784-791—1983) made competent as described by Messing in "Methods in Enzymology" vol. 101, 20-78, 1983. The transformants are selected on LB agar plates (DIFCO, Lab.) containing 50 µg/ml ampicillin and 50 µg/ml Kanamycin, at 37° C. for 24 hours.

From one of the positive clones the plasmid denominated pRTP1-8 PT-KAN having the expected characteristics is extracted. *E. coli* SM10 cells transformed with said plasmid and cultivated on LB agar at 37° C. for about 18 hours, are successively conjugated with the *Bordetella* str or nal resistant strains previously cultivated on Bordet-Gengou medium for 48 hours. The conjugation is performed on BG medium with added 10 mM MgCl2 at 37° C. for 3-6 hours. The resulting colonies are then harvested and plated on BG medium containing 30 µg/ml nalidixic acid and 50 µg/ml Kanamycin. The plates are kept at 37° C. for the purpose of selecting the strains resistant to such antibiotics. After 3 days (*B. bronchiseptica*) and 5-6 days (*B. pertussis* and *B. parapertussis*) numerous single hemolytic colonies are observed, resistant to nal and KAN, which contain in their chromosome the pRTP1-ΔPT-KAN plasmid integrated by homologous recombination with one of the regions flanking the pertussis toxin gene. In order to facilitate the recombination of also the second region, and hence the substitution of the PT chromosomal gene with the one of Kanamycin, the colonies are plated again on BG medium containing 400 µg/ml streptomycin. Operating as reported supra, strains are selected which have lost the pRTP1 plasmid imparting a sensitivity to streptomycin which is dominant to the chromosomal *Bordetella* antibiotic resistance gene.

Colonies of two types are thus obtained:

1) the ones resistant to str and nal and sensitive to Kan in which complete plasmid loss and absence of recombination has taken place and 2) the ones resistant to str, nal and Kan in which through double recombination (Δtox) the substitution of the Kanamycin gene to the PT gene has taken place.

For the purpose of confirming such chromosomal substitution, strains, Δtox W28, Δtox Tohama, Δtox 165, Δtox P14, and Δtox 7865 are characterized, operating according to known techniques, by means of Southern blot, ELISA assay and toxicity on CHO cells. In practice, the chromosomal DNA isolated from said *Bordetella* strains by the method of Marmur, J., J. Mol. Biol. (1961), 3: 208-216, is digested with suitable restriction enzymes, submitted to electrophoresis, transferred on nitrocellulose membranes and then hybridized employing as probes the 4696, bp EcoRI fragment containing the PT gene, and the DNA fragment containing the radioactively labelled KAN gene using the BRL nick-translation kit.

The hybridization reaction is performed operating according to the method of E. Southern, (1975), J. Mol. Biol., 98: 503-517. The results show the presence in the *Bordetella* Δtox strains chromosomal DNA of a DNA fragment with a molecular weight lower than that of the PT gene which hybridizes with both probes. The *Bordetella* Δtox strains are cultivated, at 37° C. for 72 hours, in SS modified medium the composition of which, in grams/liter is as follows:

Sodium L-glutamate 10.7; L-proline 0.24; NaCl 2.5; KH2 PO$_4$; KCl 0.2; MgCl$_2$×6H$_2$0 0.1; CaCl$_2$ 0.02; TRIS 6.1; L-cysteine 0.04*; FeSO$_4$×7H$_2$ 0.001*; niacin 0.004*; glutathion 0.10*; ascorbic acid 0.02*; resumin acids 10.0; 2.6-0-dimethyl beta cyclodextrin 1.0. pH 7.6.

The medium is sterilized for 20 minutes while the components marked * are sterilized separately by filtration. At regular intervals, medium samples are taken and centrifuged at 12000 rpm for four minutes at 4° C. Successively. aliquots of the acellular supernatants are assayed with the ELISA test and toxicity on CHO cells, in order to verify whether pertussis toxin is present and its toxicity. The ELISA assay, performed as described by Wong, K., H. e Skelton, S. K., J. of Clinical Microbiol., vol. 26, 1316-1320, 1988, shows that none of the Δtox strains is capable of producing detectable amounts of PT. Furthermore, the supernatants diluted 1/10, do not modify the CHO cells (Hewlett, E. L. et al., (1983), Infect. Immun. 40: 1198-1230). A non-specific toxicity is observed utilizing the undiluted supernatant.

To the end of verifying whether said strains, although not producing PT, are still capable of imparting protection against virulent *B. pertussis*, intracerebral challenge tests are carried out according to the technique described in CODE OF FEDERAL REGULATION, potency test of pertussis vaccine, 21/Par7620. In practice the Δtox W28 and Tohama strains and the same wild type strains, generally employed for the preparation of antipertussis vaccine are cultivated in 300 ml modified SS medium at 37° C. up to an optical density measured at 590 nm of 0.7. The cultures are then centrifuged at 10000 rpm for ten minutes (Beckman J21 centrifuge with J10 rotor) and the cells, separated from the supernatants, are suspended again in 50 ml saline solution and kept at 56° C. for 30 minutes. Successively, the resulting suspensions are suitably diluted as described in CODE OF FEDERAL REGULATION and utilized as conventional vaccines employing different doses. The results are reported in the following table I:

TABLE I

| dose | survival to intracerebral challenge | | | |
|---|---|---|---|---|
| ml/mouse* | Tohama | Tohama Δ tox | W28 | W28 Δ tox |
| 0.04 | 15/16 | 14/16 | 16/16 | 16/16 |
| 0.008 | 13/16 | 11/16 | 16/16 | 13/16 |
| 0.0016 | 9/16 | 6/16 | 11/16 | 8/16 |
| 0.00032 | 2/16 | 2/16 | 4/16 | 2/16 |

As one can observe from the table, although a slight protection decrease is observed for the Δtox strains, they still impart a very good protection, and, therefore. appear to be particularly suitable as antipertussis vaccines. The * indicates the volume of cellular suspension.

EXAMPLE 2

Construction of *Bordetella* Mutants Producing PT forms with Altered Toxicity

For the purpose of introducing mutagenized forms of the pertussis toxin gene in the chromosome of Δtox strains obtained as reported in Example 1, the pRTP1 plasmid is modified introducing into the BamHI site the gene encoding for the resistance to gentamycin (Pharmacia, Uppsala) or the one encoding for resistance to tetracycline (Pharmacia, Uppsala). Cloning of said genes is performed employing the recombinant DNA known techniques described by Maniatis et al. These new vectors, designated respectively pRTPO1 and pRTPT1, are then employed for introducing in the *Bordetella* chromosome the mutagenized strains of pertussis toxin. In particular, said genes are obtained by deletion or substitution mutations via site-specific mutagenesis technique, of the gene encoding the PT contained in the PT101 ATCC 67854 plasmid. More particularly, PT genes are constructed containing in the S1 nucleotide sequence the mutations reported in the first column of the following Table II.

After cloning the EcoRI fragments containing the above reported mutations in the pRTPO1 and pRTPT1 plasmids, these are employed for transforming SM10 *E. coli* cells and the thus obtained transformants are conjugated with the Δtox *Bordetella* strains. The colonies showing the integration of such plasmid in their chromosome are then selected on BG medium plates containing, repsectively, 30 μg/ml nal and 20 μg/ml gentamycin or 30 μg/ml nal and 12.5 μg/ml tetracycline. All the thus-selected colonies show the plasmid integrated in their own chromosome. Successively, to the end of selecting the plasmid loss, the colonies obtained as reported are plated on BG medium containing 400 μg/ml streptomycin. The colonies capable of growing on said medium are then simultaneously cultivated on BG plates containing respectively:

a) nal 30 μg/ml, srt 400 μg/ml and 50 μg/ml Kanamycin;

b) nal 30 μg/ml, str 400 μg/ml.

The colonies obtained in a) are those which have lost the plasmid and are therefore the same as the original Δtox colonies being still resistant to Kanamycin. The colonies grown on medium b), on the other hand, have lost the resistance to Kanamycin, the gene of which was substituted by the mutagenized one.

Figure 2:
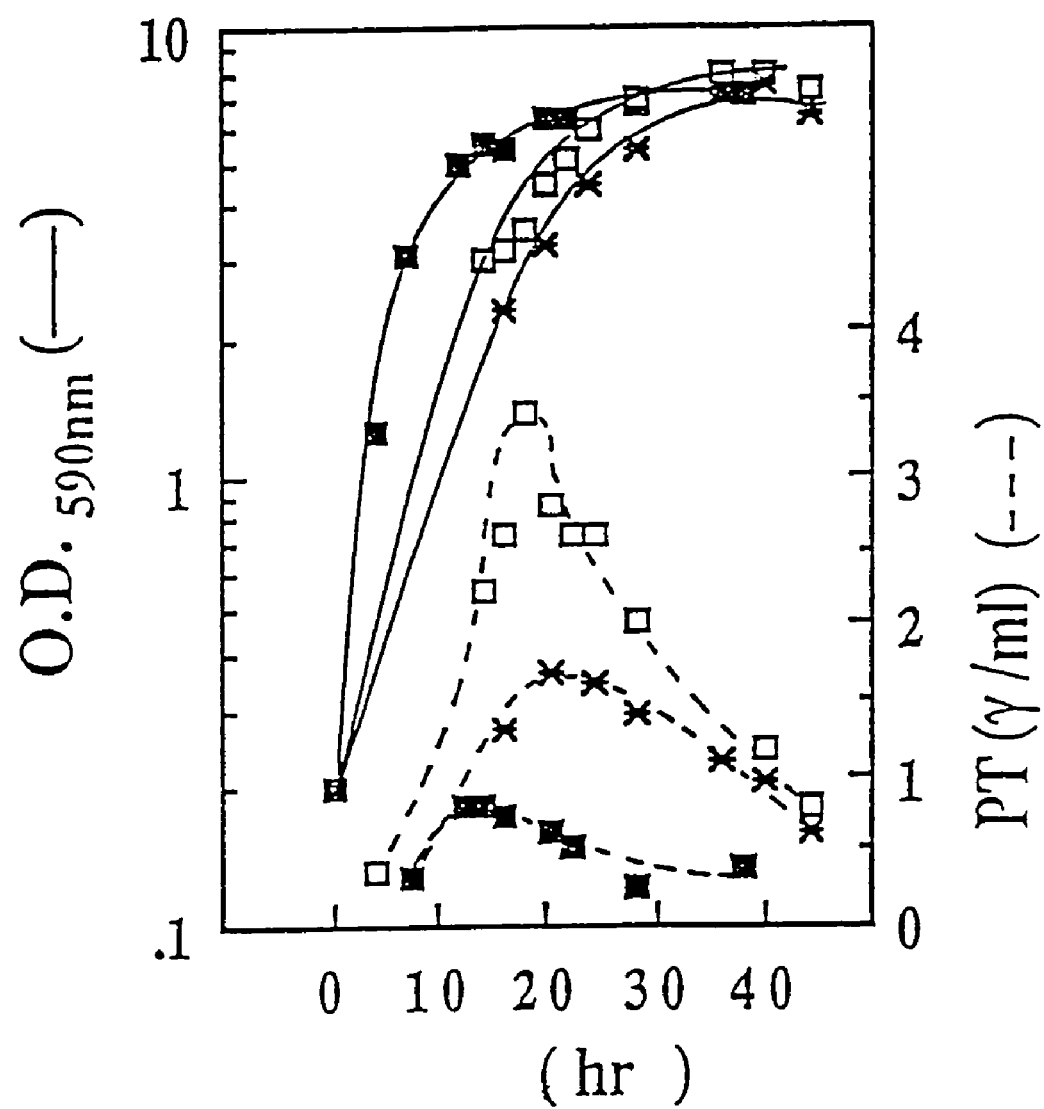
FIG. 2: the graph shows in the ordinate the optical density (O.D.) and the production of PT-129G obtained by cultivation of B. pertussis W28/PT129G (X), B. bronchiseptica 7865/PT-129G (■) and B. parapertussis P14/PT-129G (□) strains and in the abscissa the time in hours.

As an example of the capacity of the colonies obtained in b) to produce and secrete a mutant PT, the *B. pertussis* W28/PT-129G, *B. parapertussis* P14/PT-129G, and *B. bronchiseptica* 7865/PT129G strains are first expanded on BG plates and then cultivated in 15 ml modified SS medium, at 37° C. for 72 hours. The data of the PT mutant production, evaluated by monitoring with the ELISA assay, are reported in FIG. 2, and show that:—all the tested *Bordetella* strains produce the PT mutant and *B. parapertussis* produces a double amount of it with respect to other Bordetellas.

Data on production of mutant PT proteins, obtained by cultivating as reported supra *B. pertussis* W28 and BP165 and *B. parapertussis* P14 strains containing the mutant PT gene reported in the first column of Table II, are shown in the third column of the same table and indicate that:

all the tested strains are capable of expressing and secreting the PT mutants;
some of said PT mutants are produced in an amount comparable to the one obtained for the wild type PT (++++) and
B. parapertussis P14 produces a double amount of PT mutants with respect to B. pertussis.

Some of said strains (indicated with B) secrete only the oligomer B of the pertussis toxin (constituted by subunits S2, S3, S4 and S5).

The results obtained after the intracerebral challenge tests show, furthermore, that said *Bordetella* strains are suitable for the development of antipertussis cellular vaccines.

TABLE II

| PT MUTANT NAME/MUTATION | MUTATION INTRODUCED IN | | | PRODUCTION | TOXICITY CHO % | |
|---|---|---|---|---|---|---|
| | W28 | 165 | P14 | | super. | pur. |
| PT-129G<br>Glu 129 -> Gly<br>GCCAGATACCCGCTCTGG | + | + | + | ++++ | / | 5-10 |
| PT-129Asn<br>Glu 129 -> Asn<br>GTGCCAGATAATTGCTCTGGTAG | + | + | + | ++ | / | ND |
| PT-11S<br>Asp11 -> Ser<br>GGGCGGGAAGATAGCGG | + | + | + | ++++ | + | ND |
| PT-26I<br>Trp26 -> Ile<br>TTGTTTCCAATCGCCGTC | + | + | + | ++++ | 10 | ND |
| PT-9K<br>Arg9 -> Lys<br>GAGTCATATTCGTATACG | + | + | + | ++++ | 0.1 | 0.1 |
| PT-50E<br>Phe 50 -> Glu<br>TGGAGACGTCAGCGCTGT | + | + | | +/− | / | <0.0001 B |
| PT-50BAM<br>Asp-1 -> Glu Phe50 -> Glu<br>Thr53 -> Ile<br>GGGAGGATCCTCGGCCCA | | + | + | +/− | / | ND B |
| PT-13L<br>Arg13 -> Leu<br>TCCGGCGGAAGGGAGTCA | + | | + | ++++ | 30 | ND |
| PT-Δ28<br>delezione Glu 129<br>TGCCAGATAGCTCTGGTA | | + | + | ++++ | / | 5-10 |
| PT-11S/129<br>Asp11 -> Ser Glu129 -> Gly | + | | + | ++++ | / | ND |
| PT-26I/129G<br>Trp26 -> Ile Glu129 -> Gly | + | | + | ++++ | / | <0.0001 |
| PT-9K/129G<br>Arg9 -> Lys Glu129 -> Gly | + | + | + | ++++ | / | <0.0001 |
| PT-50E/129G<br>Phe50 -> Glu Glu129 -> Gly | + | | + | +/− | / | <0.0001 B |
| PT-13L/129G<br>Arg13 -> Leu Glu129 -> Gly | + | | + | ++++ | / | <0.0001 |
| PT-11S/26I<br>Asp11 -> Ser Trp26 -> Ile | + | + | | ++++ | + | ND |
| PT-11S/26I/129G<br>Asp11 -> Ser Trp26 -> Ile<br>Glu129 -> Gly | + | + | | ++ | / | <0.0001 |
| PT-11S/50E<br>Asp11 -> Ser Phe50 -> Glu | + | | | +/− | / | <0.0001 B |
| PT-11S/50E/129G<br>Asp11 -> Ser<br>Phe50 -> Glu Glu129 -> Gly | + | | | +/− | / | <0.0001 B |
| PT-26I/50E<br>Trp26 -> Ile Phe50 -> Glu | + | | | +/− | / | <0.0001 B |
| PT-26I/50E/129<br>Trp26 -> Ile Phe50 -> Glu<br>Glu 129 -> Gly | + | | | +/− | / | <0.0001 B |
| PT-13L/26I<br>Arg13 -> Leu Trp26 -> Ile | + | | | ++++ | 0.1 | 0.1 |
| PT-13L/26I/129G<br>Arg13 -> Leu Trp26 -> Ile<br>Glu129 -> Gly | + | + | | + | / | <0.0001 B |
| PT-13L/50E<br>Arg13 -> Leu Phe50 -> Glu | + | | | +/− | / | <0.0001 B |
| PT-13L/50E/129G<br>Arg13 -> Leu, Phe50 -> Glu<br>Glu129 -> Gly | + | | | +/− | / | <0.0001 B |

TABLE II-continued

| PT MUTANT NAME/MUTATION | MUTATION INTRODUCED IN | | | PRODUCTION | TOXICITY CHO % | |
|---|---|---|---|---|---|---|
| | W28 | 165 | P14 | | super. | pur. |
| PT-130G<br>Tyr130 -> Gly<br>GTGTCCAGACCTTCGCT | + | | | +++ | 5-10 | ND |
| PT-130G/129G<br>Tyr130 -> Gly Glu129 -> Gly<br>GTGTGCCAGACCCCCGCT | + | | | ++ | ND | ND |
| PT-86E<br>Gly86 -> Glu<br>TAGATGTATTCGATGAAG | + | | | +++ | 10 | ND |
| PT-88E/89S<br>Ile88 -> Glu Tyr89 -> Ser<br>CGGACTTCCGATTCGTAGCCGA | + | | | +++ | / | <0.0001<br>B |
| PT-86E/129G<br>Gly86 -> Glu Glu129 -> Gly | + | | | ++ | / | 1 |
| PT-88E/89S/129G<br>Ile88 -> Glu Tyr89 -> Ser<br>Glu129 -> Gly | + | | | | ND | ND |
| PT-8D/9G<br>Tyr8 -> Asp Arg9 -> Gly<br>GTCATAGCCGTCTACGGT | + | | | + | / | <0.0001 |
| PT-8D/9G/129G<br>Tyr8 -> Asp Arg9 -> Gly<br>Glu129→Gly | + | | | + | / | <0.0001<br>B |
| PT-44E<br>Gly44 --> Glu | + | | | ++++ | 50 | |
| PT-80/E<br>Gly80 --> Glu | + | | | ++++ | 20 | |

EXAMPLE 3

(A) Production and Purification of PT Mutants

The *B. parapertussis* P14/PT-129G, *B. pertussis* W28 9K/129G, IL pertussis W28 13L/129G and *B. pertussis* W28 26I/129G strains are cultivated in a Chemap fermentation vessel, of 30 l capacity, containing 20 l SS modified medium (pH 7.4), with an air flow of 0.1 v/v/m. The dissolved oxygen is kept at 20% varying the rotations per minute from a minimum of 200 to a maximum of 700. The temperature is controlled at 35° C. and the pH is kept within neutrality values by using a solution containing 1.5 N glutamic acid, 1.5 N hydrochloric acid, 0.15 proline N. After approximately 36-48 hours, that is when the cultures have reached an optical density measured at 590 run of 14-18, the cells are removed by centrifugation of the fermentation medium (Beckman JCF-7 centrifuge, 19000 rpm. 4° C. for 30 minutes, with a flow of 600 ml/minute) and the mutated proteins are purified from the acellular supernatant. filtered in sterile conditions (through a Durapore® cartridge (Millipore) 0.22 mμ) by absorption on Affi-Gel Blue and successive affinity chromatography on Sepharose-Fetuin® as described by Sekura R., D., et al. (J. Biol. Chem. 258: 14647-14561, 1983).

(B) Determination-of the Physico-chemical Properties of the Purified PT Mutants The physico-chemical properties of some mutant PT proteins purified as reported supra, are determined by gel electrophoresis on polyacrylamide sodium dodecyl sulphate (SDS) stained with Coomassie blue operating as described by Laemmli, N. K., (1970). Nature, 227, 680-685.

Figure 3:
FIG. 3: 15% polyacrylamide gel of PT wild type (A) toxin and of the purified mutant toxins PT-9K (B), PT-129G (C), PT-26I/129G (D), PT13L/129G (E), PT-9K/129G (F).

The results, reported in FIG. 3, show absence of contaminant proteins and a pattern identical to the one of wild type PT. A further control, performed to verify whether other contaminants were present, in particular the substances utilized in the fermentation process for the preparation of the mutant peretussis toxins, confirmed:

the absence of dimethyl (2,6-0-)beta-cyclodextrin determined according to the method described by Beeley, J. G., (1985) "Laboratory Techniques in Biochemistry and Molecular Biology", Burdon, R. H. and Van Knippennberg. P. H. (Edit.), Elsevier vol. 16);

the absence of fetuin, of 69 KD protein and of filamentous hemagglutinin, which are the possible contaminants of acellular antipertussis vaccines, determined by Western blotting analysis (Towbin, H. T. et al., (1976), P.N.A.S., USA, E:361-365) utilizing antibodies specific for said proteins;

the absence of thermonecrotic toxin, determined by the test performed on Guinea pigs as described by Kume. K. T. et al., (1986), Infect. Immun., 52: 370-377);

the absence of cyclodextrin, which is the major component of the culture medium, determined by thin layer chromatography. The PT mutants (80% yield) show a purity of 99%.

EXAMPLE 4

In Vitro Characterization of PT Mutants

A) Toxicity on CHO Cells.

The test is performed utilizing the crude and purified supernatants of cultures of some *Bordetella* strains containing the mutations reported in the first column of Table II, diluted ¹/₁₀ in DMEN medium (Flow lab., Mclean, Va.).

The results reported in the preceding Table II show a reduction in the toxicity of the pertussis toxin mutants with respect to wild type PT; the best results are obtained for mutants PT-26I/129G, PT9K/129G and PT-13L/129G for which absence of toxicity is observed ("/"=not analyzed, "ND"=not determined). Further, the non-detoxified PT-129G mutant shows, with respect to wild type pertussis toxin, a residual toxicity of 1.5-10%, while the same mutant detoxified with glutaraldehyde as described by Munoz, J. J. et al. (Infect. Immun. 32: 243-250, 1981) does not show any appreciable toxicity on CHO cells.

B) Determination of the Affinity Constant by Means of the RIA Test.

With this test the affinity constant of some PT mutants for polyclonal antibodies (anti PT goat gamma-globulins, SCLAVO S.p.A.) and monoclonal anti-S1 antibodies (1B7, described by H. Sato et al., (1984), Infect. Immun., 46:422-428) is determined. In each well of the 96 well polystyrene flat bottom microplate (Dynatech Laboratories Inc., Alexandria, Va.) are introduced 200 µl glycine buffer 5 mM pH 9.2 containing 10 µg/ml of antibodies. After one night at 4° C., the plates are saturated with 2.5% (weight/volume) of bovine albumin serum (BSA) in saline phosphate buffer (PBS) pH 8.0 and washed with 100 µl PBS containing 0.125 ml/l Tween-20. The plates are then incubated with $10^5$ cpm (counts per minute) in each well of pertussis toxin labelled with 125I. in the presence of different concentrations (0.01-0.025-0.05-0.1-0.25-0.5-1.0 µg/ml) of PT and PT mutants. After three hours at room temperature (20-25° C.). the plates are extensively washed with PBS and the incorporated radioactivity is measured in the gamma counter (Packard Inst., USA). Each sample is analyzed twice. The pertussis toxin is labelled with radioactive iodine by the standard chloramine T method (BDH Chem., England) operating according to the instructions of the supplying firm. The results, reported in the following table III, show that all the PT mutants maintain the recognized epitope of the monoclonal 1B7 antibody and they are recognized as having high affinity from pertussis antitoxin goat gamma-globulins and therefore capable of neutralizing the PT toxin.

TABLE III

| PT Mutants | AFFINITY CONSTANT (Ka(L/mol)) | |
| --- | --- | --- |
| | MAb 1B7 | anti-PT goat immunoglobulines |
| PT | $3.5 \times 10^8$ | $5.0 \times 10^{10}$ |
| PT-129G | $2.1 \times 10^8$ | $1.7 \times 10^{10}$ |
| PT-9K | $8.9 \times 10^8$ | $1.0 \times 10^{10}$ |
| PT-13L/129G | $1.3 \times 10^8$ | $1.3 \times 10^{10}$ |
| PT-26I/129G | $5.5 \times 10^7$ | $8.9 \times 10^9$ |
| PT-9K/129G | $3.3 \times 10^8$ | $1.2 \times 10^{10}$ |

EXAMPLE 5

In Vivo Characterization of PT Mutants

The biological properties of some PT mutants and the possibility of their use in an antipertussis vaccine were tested by means of:

a) Intracerebral Challenge

The test is performed utilizing the standard cellular vaccine (control) and the PT-129G mutants, as such and detoxified with glutaraldehyde (PT-129G Det) and PT-26I/129G. The results are shown in Table IV.

TABLE IV

| Standard cellular vaccine | | Purified PT mutants | |
| --- | --- | --- | --- |
| Dose ml/mouse | survival | dose microg/mouse | survival |
| | | PT-129G | PT-129GDet. |
| 0.04 | 15/16 | 30.0 | 0/16* | 12/16 |
| 0.008 | 11/16 | 20.0 | 3/16* | 13/16 |
| 0.0016 | 8/16 | 15.0 | 5/16* | 12/16 |
| 0.00032 | 0/16 | 7.5 | 9/16 | 9/16 |
| | | 3.75 | 3/16 | 7/16 |
| | | 1.8 | 1/16 | 13/16 |
| | | 0.9 | 1/16 | 11/16 |
| | | PT-26I/129G | |
| | | 30.00 | 16/16 |
| | | 12.00 | 16/16 |
| | | 4.80 | 16/16 |
| | | 1.92 | 15/16 |
| | | 0.77 | 11/16 |

The low survival (*) obtained utilizing PT-129G is due to the mutant residual toxicity which is approximately 1-2% of the one of PT toxin.

b) Leucocytosis

Groups of 4 female Balb/C mice of 7-8 weeks age, weighing approximately 20 g are treated by endovenous injection at day 0, with 0.2 ml physiological (saline) sterile apyrogen solution as such (control) or containing:

(0.004-0.02-0.04-0.1-0.5 and 1.0. µg/mouse) of PT.

(0.1-0.5-2.5-µg/mouse) of PT-13L;

(0.1-0.5-2.5-12.5-25.0 and 50.0 µg/mouse) of PT9K, PT-129G, PT-129G detoxified, PT-26I/129G, PT-13L/129G and PT9K/129G.

Figure 4:
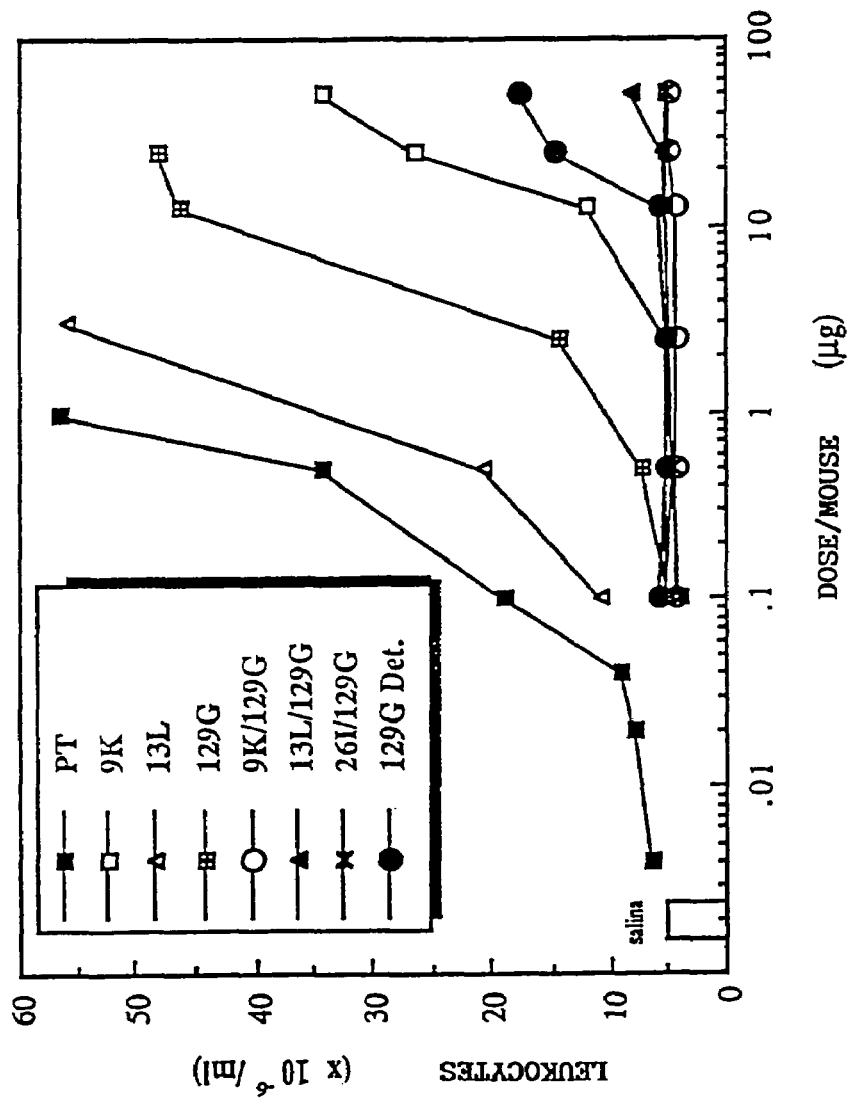
FIG. 4: the graph shows in the abscissas the dose of PT and of PT mutants expressed as pg/mouse and in the ordinate the number of leucocytes×10$^6$ ml.

After three days, the mice are bled and the number of total mononucleated cells (PBMC)/ml peripheral blood is counted individually in turk solution (0.01% gentian violet and 3% acetic acid). A portion of peripheral blood for each mouse, previously treated with a solution to lyse red corpuscles, is then analyzed by FACS (Fluorescence Activated Cell Sorter) to measure the percentage increase of lymphocytes and of polymorphonucleated cells in the mice treated with the different toxins, with respect to the controls. The results reported in FIG. 4, show, in general, a reduction of the PT mutant toxicity with respect to PT, which reaches values lower than 0.01% for mutants PT-26I/129G, PT-9K/129G and PT13L/129G.

The same test is performed on groups of Balb/C mice by intraperitoneal injection on day 0 of 0.5 ml physiological sterile solution as such, or containing PT or the PT-9K/129G mutant toxin in the same concentrations reported above. Three days after the administration, blood samples are taken from the animal orbital plexus and tested as reported supra. The results, expressed as average +/− the standard deviation of leucocytes counts from 5 animals individually tested, are reported in FIG. 4 and in Table V relatively to PT and PT-9K/129G.

TABLE V

| Antigene | Dose microg/mouse | Leukocytosis (PBMC/ml × $10^{-6}$) |
| --- | --- | --- |
| Saline | — | 5.23 +/− 0.51 |
| PT | 0.004 | 5.94 +/− 0.41 |
| | 0.020 | 10.33 +/− 0.82 |
| | 0.040 | 14.34 +/− 0.83 |

TABLE V-continued

| Antigene | Dose microg/mouse | Leukocytosis (PBMC/ml × $10^{-6}$) |
|---|---|---|
| | 0.100 | 17.73 +/− 1.12 |
| | 0.500 | 45.73 +/− 3.76 |
| | 1.000 | 55.19 +/− 6.62 |
| PT-9K/129G | 2.500 | 4.45 +/− 0.41 |
| | 12.500 | 4.39 +/− 0.32 |
| | 25.000 | 4.79 +/− 0.44 |
| | 50.000 | 4.71 +/− 0.35 |

N.D. = not determined c) Histamine Sensitivity

Groups of 5 female Balb/C mice of 7-8 weeks age, weighing approximately 20 g are intraperitoneally inoculated on day 0 with ml physiological saline sterile apyrogen solution as such (control), or containing different doses of PT, of PT-129G as such or detoxified with glutaraldehyde (PT-129G Det.), of PT-9K and PT9K/129G. Six days after the administration, the mice are intraperitoneally inoculated with 0.5 ml physiological sterile apyrogen solution containing 4 mg/mouse histamine dihydrochloride (Sigma Chemical Company, St. Louis, Mo.).

Deaths are registered 24 hour after the histamine administration.

The results are reported in the following tables VI and VII

TABLE VI

| DAY 0 | | DAY +6 | DEAD/TOTAL |
|---|---|---|---|
| dose/mouse 0.5 ml/i.p. | | dose/mouse 0.5 ml/i.p. histamine (4 mg) | |
| saline | | dose/mouse 0.5 ml/i.p. histamine (4 mg) | 0/5 |
| PT | 0.050 × $10^{-3}$ µg | dose/mouse 0.5 ml/i.p. histamine (4 mg) | 0/5 |
| " | 0.500 × $10^{-3}$ µg | dose/mouse 0.5 ml/i.p. histamine (4 mg) | 0/5 |
| " | 5.000 × $10^{-3}$ µg | dose/mouse 0.5 ml/i.p. histamine (4 mg) | 0/5 |
| " | 50.000 × $10^{-3}$ µg | dose/mouse 0.5 ml/i.p. histamine (4 mg) | 0/5 |
| " | 100.000 × $10^{-3}$ µg | dose/mouse 0.5 ml/i.p. histamine (4 mg) | 0/5 |
| " | 500.000 × $10^{-3}$ µg | dose/mouse 0.5 ml/i.p. histamine (4 mg) | 0/5 |
| " | 1.000.000 × $10^{-3}$ µg | dose/mouse 0.5 ml/i.p. histamine (4 mg) | 3/5 |
| PT-129G | 0.0005 µg | dose/mouse 0.5 ml/i.p. histamine (4 mg) | 0/5 |
| " | 0.0050 µg | dose/mouse 0.5 ml/i.p. histamine (4 mg) | 0/5 |
| " | 0.0500 µg | dose/mouse 0.5 ml/i.p. histamine (4 mg) | 0/5 |
| " | 0.5000 µg | dose/mouse 0.5 ml/i.p. histamine (4 mg) | 0/5 |
| " | 5.0000 µg | dose/mouse 0.5 ml/i.p. histamine (4 mg) | 0/5 |
| " | 50.0000 µg | dose/mouse 0.5 ml/i.p. histamine (4 mg) | 5/5 |
| PT-129G Det | 0.0005 µg | dose/mouse 0.5 ml/i.p. histamine (4 mg) | 0/5 |
| " | 0.0050 µg | dose/mouse 0.5 ml/i.p. histamine (4 mg) | 0/5 |
| " | 0.0500 µg | dose/mouse 0.5 ml/i.p. histamine (4 mg) | 0/5 |
| " | 0.5000 µg | dose/mouse 0.5 ml/i.p. histamine (4 mg) | 0/5 |
| " | 5.0000 µg | dose/mouse 0.5 ml/i.p. histamine (4 mg) | 0/5 |
| " | 50.0000 µg | dose/mouse 0.5 ml/i.p. histamine (4 mg) | 0/5 |

TABLE VII

| DAY 0 | | DAY +6 | DEAD/TOTAL |
|---|---|---|---|
| Dose/mouse 0.5 ml i.p. | | dose/mouse 0.5 ml i.p. histamine (4 mg) | |
| saline | | dose/mouse 0.5 ml i.p. histamine (4 mg) | 0/5 |
| PT | 0.010 µg | dose/mouse 0.5 ml i.p. histamine (4 mg) | 0/5 |
| " | 0.050 µg | dose/mouse 0.5 ml i.p. histamine (4 mg) | 0/5 |
| " | 0.100 µg | dose/mouse 0.5 ml i.p. histamine (4 mg) | 0/5 |
| " | 0.500 µg | dose/mouse 0.5 ml i.p. histamine (4 mg) | 1/5 |
| " | 1.000 µg | dose/mouse 0.5 ml i.p. histamine (4 mg) | 4/5 |
| " | 5.000 µg | dose/mouse 0.5 ml i.p. histamine (4 mg) | 5/5 |
| PT-9K | 0.100 µg | dose/mouse 0.5 ml i.p. histamine (4 mg) | 0/5 |
| " | 0.500 µg | dose/mouse 0.5 ml i.p. histamine (4 mg) | 0/5 |
| " | 1.000 µg | dose/mouse 0.5 ml i.p. histamine (4 mg) | 0/5 |
| " | 5.000 µg | dose/mouse 0.5 ml i.p. histamine (4 mg) | 0/5 |
| " | 50.000 µg | dose/mouse 0.5 ml i.p. histamine (4 mg) | 5/5 |
| PT-9K/129G | 0.100 µg | dose/mouse 0.5 ml i.p. histamine (4 mg) | 0/5 |
| " | 0.500 µg | dose/mouse 0.5 ml i.p. histamine (4 mg) | 0/5 |
| " | 1.000 µg | dose/mouse 0.5 ml i.p. histamine (4 mg) | 0/5 |

TABLE VII-continued

| DAY 0 | | DAY +6 | | DEAD/TOTAL |
|---|---|---|---|---|
| " | 2.500 µg | dose/mouse 0.5 ml i.p. histamine (4 mg) | | 0/5 |
| " | 5.000 µg | dose/mouse 0.5 ml i.p. histamine (4 mg) | | 0/5 |
| " | 7.500 µg | dose/mouse 0.5 ml i.p. histamine (4 mg) | | 0/5 |
| " | 12.500 µg | dose/mouse 0.5 ml i.p. histamine (4 mg) | | 0/5 |
| " | 25.000 µg | dose/mouse 0.5 ml i.p. histamine (4 mg) | | 0/5 |
| " | 50.000 µg | dose/mouse 0.5 ml i.p. histamine (4 mg) | | 0/5 | d) Anaphylaxis

Potentiation of the anaphylactic sensitivity is determined according to the method described by Steinman L. et al., (1985), P.N.A.S. USA, 82:8733-8736. Groups of five female Balb/C mice of 7-8 weeks age (H-$2^d$ weighing approximately 20 g, are intraperitoneally inoculated on days −1, +1 and +6 with 0.2 ml physiological saline sterile apyrogen solution as such (control), or containing bovine serum albumine (BSA) (Sigma Chemical Company, St. Louis, Mo.). The same groups of mice are then endovenously inoculated on days 0 and +2 with 0.4 ml apyrogen sterile saline solution as such, or containing 40, 100 and 500 ng/mouse of PT, 100, 500 and 2500 ng/mouse PT-129G as such or detoxified with glutaraldehyde (PT-129G Det.) or 500, 2500 and 7500 ng/mouse of PT-9K/129O. Deaths are registered after two hours after the last BSA administration.

The results are reported in Table VIII.

TABLE VIII

| DAY −1 Dose/ mouse 0.2 ml i.p | DAY 0 Dose/ mouse 0.4 ml i.v. | DAY +1 Dose/ mouse 0.2 ml i.p. | DAY +2 Dose/ mouse 0.4 ml i.v. | DAY +6 Dose/ mouse 0.2 ml i.p. | dead/total |
|---|---|---|---|---|---|
| Saline | Saline | Saline | Saline | Saline | 0/5 |
| BSA 1 mg | Saline PT | BSA 1 mg | Saline PT | BSA 1 mg | 0/5 |
| Saline | 40 ng | Saline | 40 ng | Saline | 0/5 |
| BSA 1 mg | 40 ng | BSA 1 mg | 40 ng | BSA 1 mg | 4/5 |
| Saline | 100 ng | Saline | 100 ng | Saline | 0/5 |
| BSA 1 mg | 100 ng | BSA 1 mg | 100 ng | BSA 1 mg | 4/5 |
| Saline | 500 ng | Saline | 500 ng | Saline | 0/5 |
| BSA 1 mg | 500 ng PT-129G | BSA 1 mg | 500 ng PT-129G | BSA 1 mg | 5/5 |
| Saline | 100 ng | Saline | 100 ng | Saline | 0/5 |
| BSA 1 mg | 100 ng | BSA 1 mg | 100 ng | BSA 1 mg | 0/5 |
| Saline | 500 ng | Saline | 500 ng | Saline | 0/5 |
| BSA 1 mg | 500 ng | BSA 1 mg | 500 ng | BSA 1 mg | 1/5 |
| Saline | 2.500 ng | Saline | 2.500 ng | Saline | 0/5 |
| BSA 1 mg | 2.500 ng PT-129G Det | BSA 1 mg | 2.500 ng PT-129G Det | BSA 1 mg | 3/5 |
| Saline | 100 ng | Saline | 100 ng | Saline | 0/5 |
| BSA 1 mg | 100 ng | BSA 1 mg | 100 ng | BSA 1 mg | 0/5 |
| Saline | 500 ng | Saline | 500 ng | Saline | 0/5 |
| BSA 1 mg | 500 ng | BSA 1 mg | 500 ng | BSA 1 mg | 0/5 |
| Saline | 2.500 ng | Saline | 2.500 ng | Saline | 0/5 |
| BSA 1 mg | 2.500 ng PT-9K/ 129G | BSA 1 mg | 2.500 ng PT-9K/ 129G | BSA 1 mg | 0/5 |
| Saline | 500 ng | Saline | 500 ng | Saline | 0/5 |
| BSA 1 mg | 500 ng | BSA 1 mg | 500 ng | BSA 1 mg | 0/5 |
| Saline | 2.500 ng | Saline | 2.500 ng | Saline | 0/5 |
| BSA 1 mg | 2.500 ng | BSA 1 mg | 2.500 ng | BSA 1 mg | 0/5 |
| Saline | 7.500 ng | Saline | 7.500 ng | Saline | 0/5 |
| BSA 1 mg | 7.500 ng | BSA 1 mg | 7.500 ng | BSA 1 mg | 0/5 | e) IAP (Islet Activating Protein)

The activation of pancreatic islets by PT or by PT-9K/129G is determined as describe by Kreeftenberg, J. G. et al. (1984), J. Biol. Stand., 12:151-157. Groups of 5 female Balb/C mice of 5-7 week age weighing approximately 20 g are intraperitoneally inoculated with 0.2 ml apyrogen sterile saline solution as such (control), or containing 25 µg/ml PT9K/129G or 1 µg/ml PT. After 4 days the insulin levels in the mice sera expressed as mU/l are determined.

The results show, as expected, a significant increase of insulin secretion (19.6 mU/l) induced by PT, while the values of the secretion induced by the PT-K/129G mutants (5 mU/l) are comparable to the ones obtained with the control (8 mU/l).

EXAMPLE 6

Formaldehyde Treatment of PT-9K/129G Mutant a) Study of the Effect of the Treatment on the Mitogenicity, Hemagglutinating Activity and Affinity Constant of Mutant PT-9K/129G.

Figure 5:
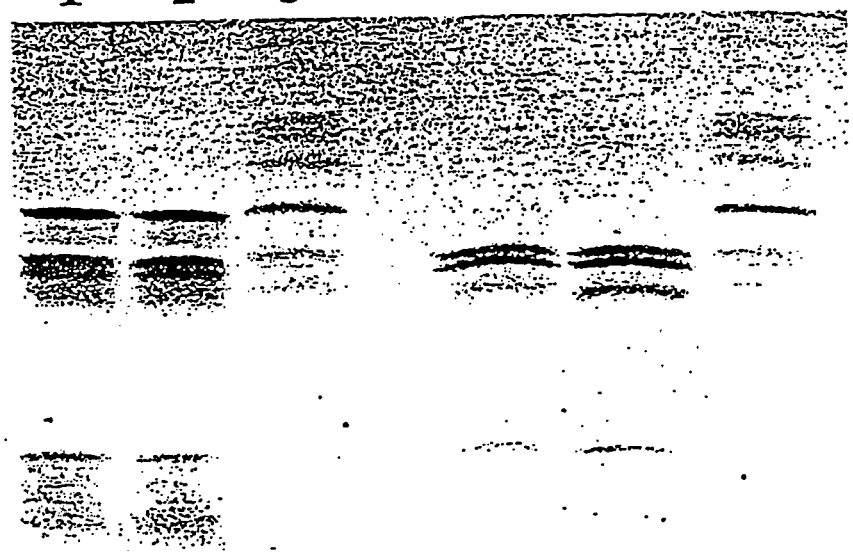
FIG. 5: electrophoretic pattern of wild type PT (lanes 1,4), of the PT-gK/129G non-stabilized mutant (lanes 2, 5) of the same mutant stabilized with formaldehyde (PTF-9K/129G) (lanes 3 and 6) at day 0 (lanes 1,2,3) and after 1 month at 37° C. (lanes 4,5,6).

Mutant PT-9K/129G purified as reported in example 3. is dialysed against (PBS), pH 7.4, containing 0.025 lysine (Ajinomoto, Japan) and 0.01% merthiolate (ELANCO, USA), for 24 hours at 4° C. and then suspended again in PBS. After determination of the protein contents (Lowry, O. H. et al., (1951). J. Biol. Chem., IU:265-275). aliquotes of the mixture are added at different concentrations (0.035% to 0.420% w/v) of formaldehyde (4% solution in PBS, pH 7.4) so as to obtain a final ratio (weight/weight) mutant to formaldehyde of between 0.300 and 0.025. The resulting mixtures are incubated at 37° C. for 48 hours, in the absence and in the presence of 0.025 M lysine, and then repeatedly dialysed against PBS. The mixtures are then tested to determine their free formaldehyde contents which is found to be lower than 0.01% (weight/volume). Furthermore, the mixture, analysed on SDS-PAGE, show the same electrophoretic pattern as PT and the presence of some extra bands one of which migrates with subunits S2 and S3 and the other, with higher molecular weight, with subunit S1 (FIG. 5, lane 3).

Figure 6:
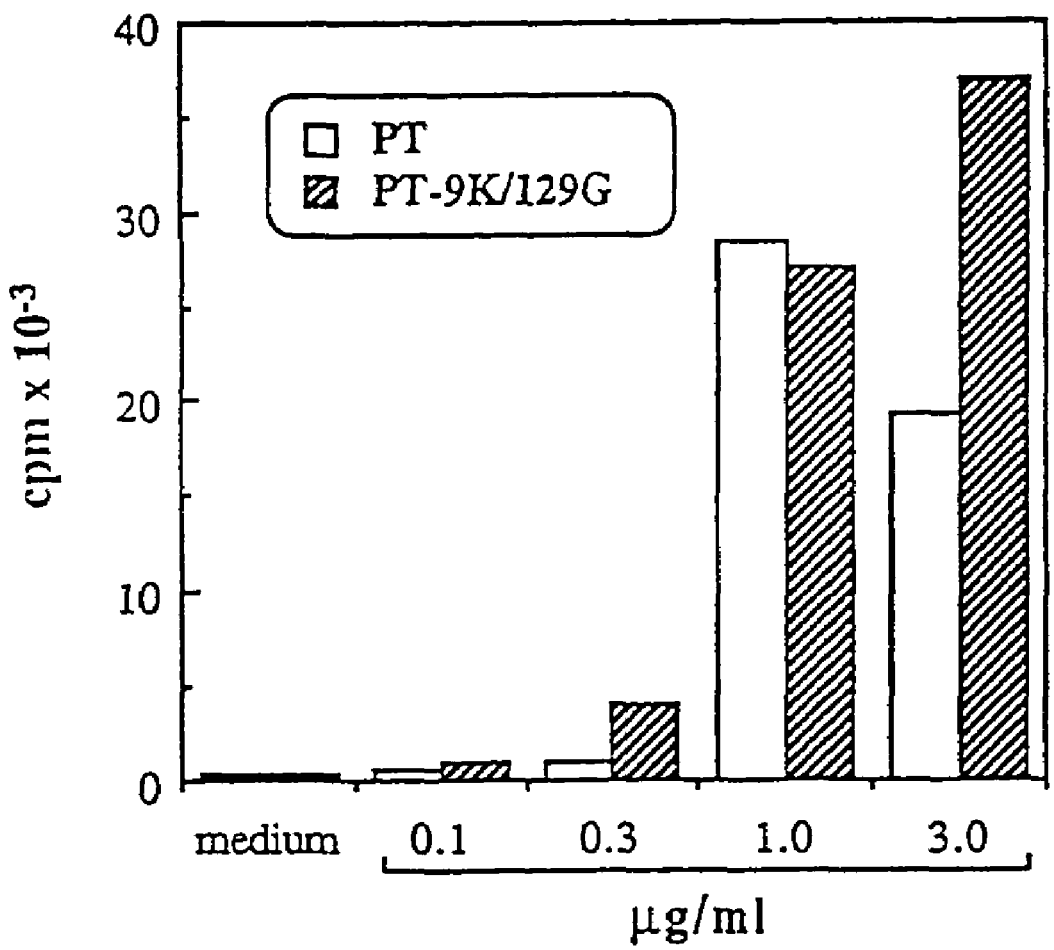
FIG. 6: shows the PBMC mitogenic response to wild type PT and to the PT-9K/129G mutant. The PBMC utilized in this test do not show any significant antigen-specific response vs. heat inactivated PT. The standard deviations were lower than 15%.
Figure 7:
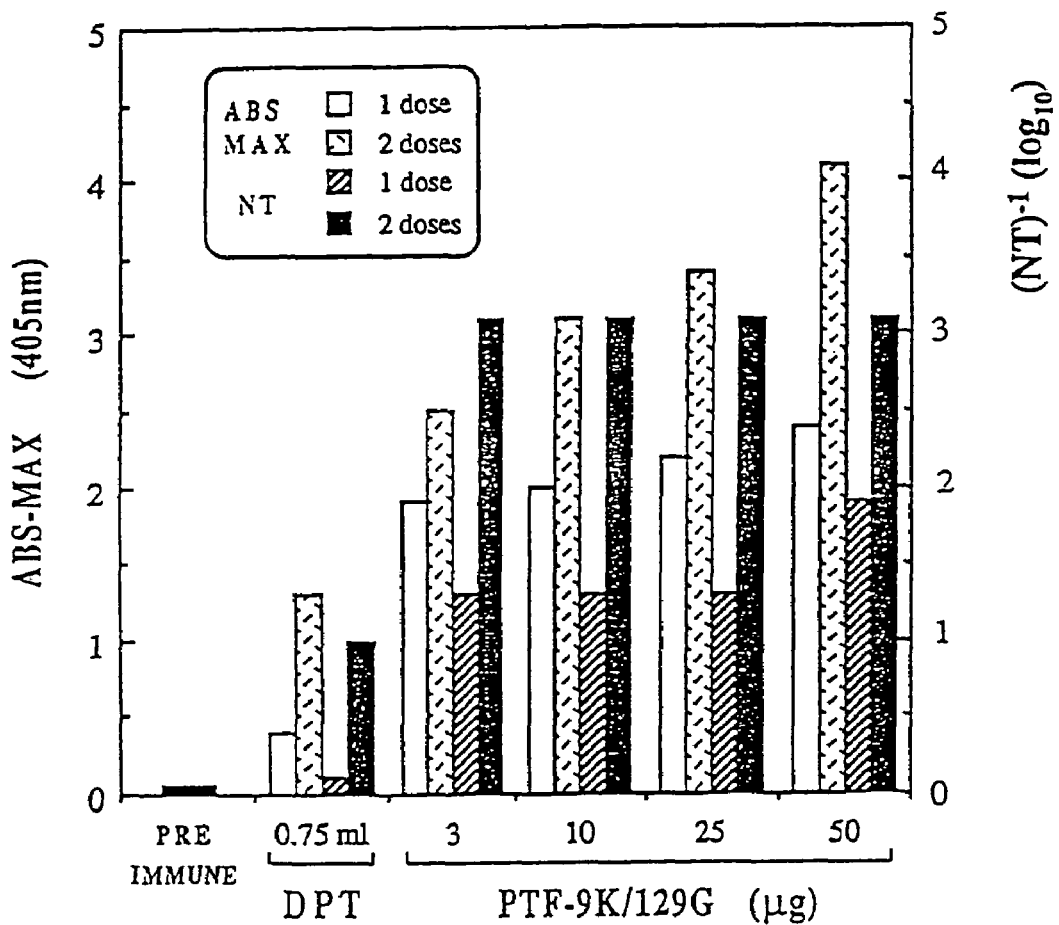
FIG. 7: shows the antibody titer (ELISA assay) and the neutralizing capacity of antibodies obtained in guinea pigs after 1 or 2 s.c. injections of PT or of different doses of PTF-9K/129G adsorbed on AL(OH)$_3$. The antibody antitoxin levels are expressed as values of maximum absorbance of undiluted sera (ABS-MAX). The neutralizing titers (NT) are expressed as the reciprocal of the highest serum dilution capable of inducing 100% inhibition of the agglutinating effect on the CHO cells induced by 120 pg PT assayed in triplicate.
Figure 8:
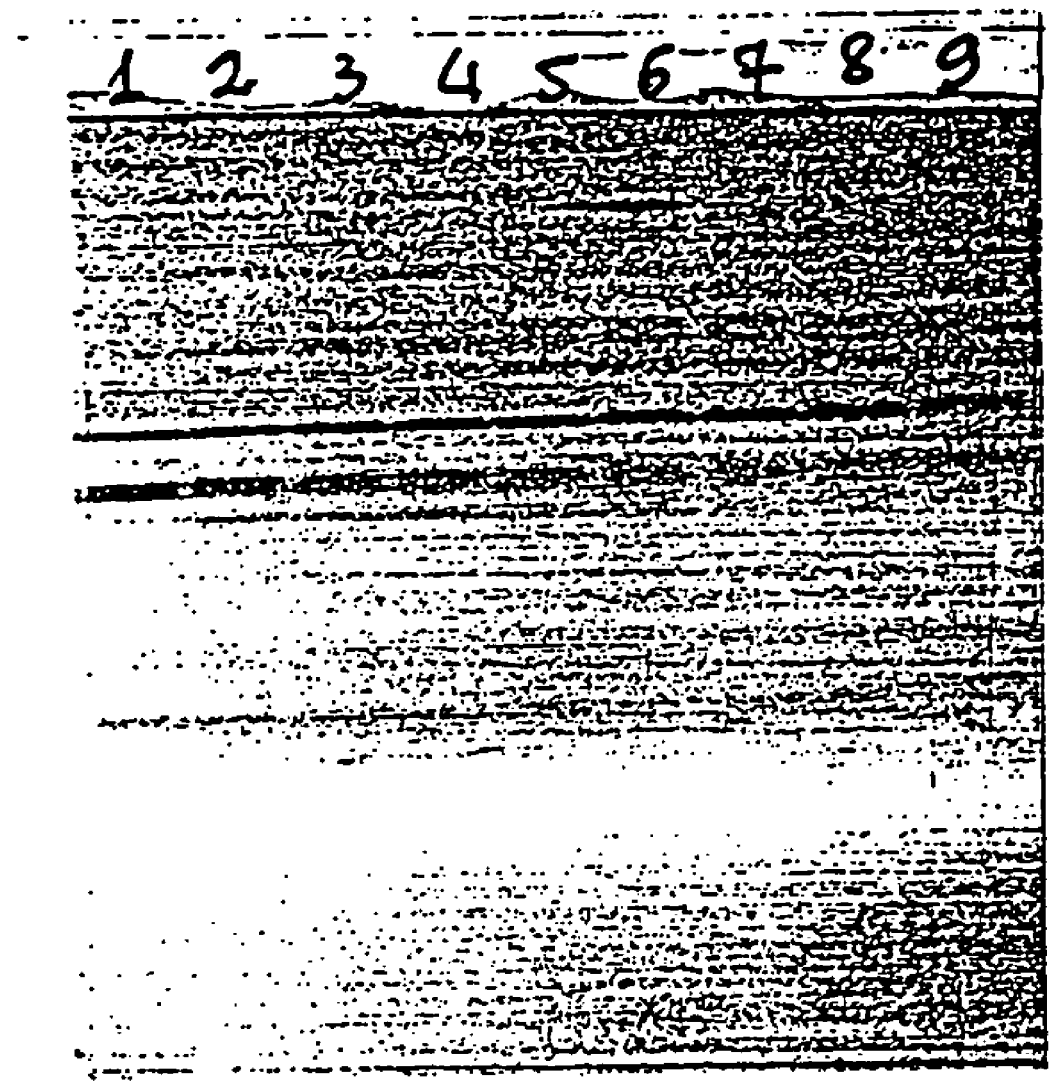
FIG. 8: electrophoresis on polyacrylamide SDS gel of PT-gK/129G specimens treated with different percent concentrations of formaldehyde (0.035, 0.042, 0.052, 0.070, 0.105, 0.140, 0.210 and 0.420%).

The mitogenic activity of the PT-9K/129G mutant treated with different concentration of formaldehyde (PTF-9K/129G) is then determined by measuring the proliferative response of human peripheral blood mononucleated cells (PBMC) isolated from normal adults and compared with the response to wild-type PT and to the same mutant as such (FIG. 6). In practice, the PBMC cells are plated in wells of 96 flat bottom well microplates (Costar, Cambridge, 14A) at a concentration of $10^5$/well in 0.2 ml of RPMI 1640 (Gibco Laboratories, Paisley) supplemented with 2 mM L-glutamine, 1% non-essential amino acids, $10\times10^{-5}$ M 2-mercaptoethanol and 10% human serum albumin. PT and the PTF-9K/129G and PT-9K/129G mutant toxins are then added in each well at a concentration of 0.1, 0.3. 1.0 and 3.0 and 6.0 μg/ml. After 96 hours incubation at 37° C., in each well are introduced 1 microci ($^3$H) thymidine (sp. act. 185 GBq/mmole; Amersham International, Amersham UK). After 16 hours at room temperature, the cells are collected on glass wool filters with a cell collector (Skatron, Lier, Norway) and the incorporated radioactivity determined by liquid scintillation. The results reported in FIG. 6 (PT, PT-9K/129G) and table IX (PT9K/129G and PTF-9K/129G) show that:

- the PT-9K/129G mutant maintains a mitogenic activity against human T lymphocytes comparable to that of wild-type PT protein. This is in accordance with the observation that said mitogenic activity is due to the presence of B oligomer;
- that increasing formaldehyde concentrations reduce, to disappearance, the mitogenic activity.

The hemagglutinating activity of mutant PTF-9K/129G is determined as described by Sato et al., (1983) Infect. Immun., 41:313-320, utilizing as target cells chicken red blood cells fixated with glutaraldehyde. The results reported in Table IX indicate that the treatment with increasing formaldehyde doses progressively reduces the hemagglutinating activity of the mutant.

The affinity constant in determined as described in the preceding Example 4. The results are reported in Table IX where:

constant. The same molecules, kept at 37° C. for thirty days, show instead a progressive decrease of the intensity of the band corresponding to the S1 subunit for PT and the PT-9K/129G mutant (FIG. 5, lanes 4 and 5), which is not observed for the PTF-9K/129G mutant (FIG. 5, lane 6).

TABLE X

| | days | Conservation temperature | Affinity |
|---|---|---|---|
| PT (A) | 0 | 4° C. | $2.0 \times 10^{10a}$ |
| PT (B) | 0 | 4° C. | $2.4 \times 10^8$ |
| PT-9K/129G (A) | 0 | 4° C. | $9.8 \times 10^9$ |
| PT-9K/129G (B) | 0 | 4° C. | $6.1 \times 10^8$ |
| PTF-9K/129G (A) | 0 | 4° C. | $1.7 \times 10^{10}$ |
| PTF-9K/129G (B) | 0 | 4° C. | $3.2 \times 10^8$ |
| PT (A) | 120 | 4° C. | N.D.[b] |
| PT (B) | 120 | 4° C. | N.D. |
| PT-9K/129G (A) | 120 | 4° C. | $9.5 \times 10^9$ |
| PT-9K/129G (B) | 120 | 4° C. | $5.7 \times 10^8$ |
| PTF-9K/129G (A) | 120 | 4° C. | $1.4 \times 10^{10}$ |
| PTF-9K/129G (B) | 120 | 4° C. | $6.2 \times 10^8$ |
| PT (A) | 120 | 20° C. | N.D. |
| PT (B) | 120 | 20° C. | N.D. |
| PT-9K/129G (A) | 120 | 20° C. | $3.1 \times 10^{10}$ |
| PT-9K/129G (B) | 120 | 20° C. | $2.9 \times 10^8$ |
| PTF-9K/129G (A) | 120 | 20° C. | $1.5 \times 10^{10}$ |
| PTF-9K/129G (B) | 120 | 20° C. | $2.1 \times 10^8$ | where:

a) the data, evaluated by means of non-linear regression analysis, are expressed as Ka(L/Mol) and represent the geo-

TABLE IX

| FORMALDEHYDE | | MITOGENICITY[a] | | | | HEMOAGGLUTINATIO[b] | AFFINITY[c] [Ka(L/Mol)] | |
|---|---|---|---|---|---|---|---|---|
| (dose) | | (μg/ml) | | | | | | |
| (%)[d] | PT/F[e] | 6 | 3 | 1 | 0.3 | (μg/well) | gamma-globulines | mAB(1B7) |
| — | — | 52.0 | 35.0 | 23.0 | 12.0 | 0.5-1 | $1.15 \times 10^9$ | $5.54 \times 10^7$ |
| 0.035 | 0.300 | 51.4 | 51.2 | 43.6 | 15.4 | 4 | $1.61 \times 10^9$ | $7.4 \times 10^7$ |
| 0.042 | 0.250 | 45.8 | 37.0 | 30.1 | 10.1 | 4 | $1.67 \times 10^9$ | $5.04 \times 10^7$ |
| 0.052 | 0.200 | 15.6 | 48.3 | 29.6 | 10.7 | 4 | $8.25 \times 10^9$ | — |
| 0.070 | 0.150 | 49.5 | 42.1 | 11.8 | 2.1 | 4 | N.D. | — |
| 0.105 | 0.100 | 33.1 | 19.8 | 4.7 | 0.9 | 9 | $1.85 \times 10^8$ | — |
| 0.140 | 0.075 | 17.4 | 13.5 | 2.6 | 0.6 | >10 | $1.03 \times 10^8$ | — |
| 0.210 | 0.050 | 12.4 | 11.3 | 2.0 | 0.3 | >10 | $5.60 \times 10^7$ | — |
| 0.420 | 0.025 | 3.3 | 1.5 | 0.5 | 0.6 | >10 | $6.75 \times 10^7$ | — |

[a] the results are expressed as average of counts per minute (cpm $\times 10^{-3}$) for each culture tested in duplicate;
[b] the results are expressed as the protein dose which causes complete agglutination of the chicken red blood cells fixated with glutaraldehyde;
[c] the affinity constant is determined by RIA test;
[d] the percentage (weight/volume) formaldehyde in the sample is reported;
[e] indicates the mutant/formaldehyde ratio (weight/weight) in the sample.

B) Study of the Formaldehyde Treatment on the PT-9K/129G Stability.

PT, the mutant PT-9K/129G as such and the same mutant treated with 0.035% (W/v) formaldehyde (PTF-9K/129G) are kept at 4°, 20° and 37° C. Then the proteins are tested after 120 days (4° C. and 20° C.) and 30 days (37° C.) to determine the electrophoretic profile and the affinity constant against polyclonal (anti-PT gamma globulins) (A) antibodies and monoclonal (1B7) (B) antibodies.

The results (Table X and FIG. 5) indicate that the molecules kept at 4° C. and 20° for a period of 120 days do not undergo any variation of their electrophoretic pattern or their affinity metric average of the value obtained for a sample tested in triplicate. Standard deviation values are never higher than 15%.

b) N.D.=Not determined.

C) Analysis of the Amino Acid Composition.

The analysis of the amino acid residues of mutant PT-9K/129G is performed, before and after the treatment with 0.035% formaldehyde, as described by Spackman D. H. et al., (1958) Anal. Chem., 30:11901206. The acid hydrolysis of PT mutants is performed in 6N HCl at 110° C. for 24 hours in vials sealed under vacuum. The amino acid analysis is then performed employing an amino acid analysis apparatus (Kontron, Zurich, Switzerland). During the acid hydrolysis the tryptophan amino acid residue is destroyed and therefore it was not possible to determine it. Further, because of deamidation during the acid hydrolysis, asparagine and glutamine are transformed respectively in aspartic acid and glutamic acid, in Table XI are reported the values corresponding to the sum of asparagine+aspartic acid (Asx) and glutamine+glutamic acid (Glx).

The results are reported in Table XI.

TABLE XI

| Amminoacids | PT | PT-9K/129G | PFT-9K/129G |
|---|---|---|---|
| Asx | 65 | 61.2 | 67.0 |
| Thr | 70 | 70.5 | 65.6 |
| Ser | 67 | 70.1 | 61.4 |
| Glx | 82 | 60.1 | 93.5 |
| Pro | 55 | N.D.[b] | N.D. |
| Gly | 80 | 81.3 | 85.5 |
| Ala | 87 | 79.8 | 90.0 |
| Cys | 26 | N.D. | N.D. |
| Val | 67 | 72.9 | 67.9 |
| Met | 29 | 28.8 | 26.7 |
| Ile | 40 | 40.0 | 38.0 |
| Leu | 74 | 75.8 | 77.3 |
| Tyr | 62 | 63.5 | 61.2 |
| Phe | 32 | 30.5 | 31.0 |
| Lys | 32 | 39.3 | 164.9[c] / 14.6 |
| His | 16 | 16.7 | 14.6 |
| Arg | 62 | 63.5 | 65.0 |
| Trp | 6 | N.D. | N.D. | where:
a) the theoretical values deduced from the primary protein structure expressed as amino acid/protein ratio;
b) N.D.=not determined
c) the underlined value shows the lysine increment after formaldehyde treatment in the presence 0.025 M lysine.

EXAMPLE 7

Toxicity of the PTF-9K/129G Mutant on Cho Cells $1 \times 10^4$ CHO cells are incubated for 48 hours with different PTF-9K/129G doses (between 0.01 and 5 µg/ml) and PT doses (between 0.3 pg and 90 ng/ml). Then the minimum dose is determined which is capable of causing the morphological change of the cells. The results show that the PTF-9K/129G mutant is devoid of toxicity at the maximum tested dose (5 µg/ml) and is at least $10^6$ times less toxic than PT (5 pg/ml).

EXAMPLE 8

In Vivo Characterization of the Biological Properties of the PTF-9K/129G Mutant

A) Anaphylaxis Potentiation

The induction of anaphylactic sensitivity is determined according to the method described by Steinman, L. et al. (1985) P.N.A.S USA, 82: 8733-8736. Groups of 5 female Balb/C mice of 5-7 weeks, weighing approximately 20 g. were intraperitoneally inoculated, on days −1. +1 and +6, with 0.2 ml physiological sterile apyrogenous saline solution as such, or containing 1 mg/mouse BSA (Sigma Chemical Company, St. Louis, Mo.). The same groups of mice were then treated endovenously on days 0 and +2 with 0.2 ml apyrogen sterile saline as such, or containing 0.04, 0.1 and 0.5 µg/mouse of PT or 2.5 and 7.5 Mg/mouse PTF-9K/129C.

Deaths were registered 2 hours after the last BSA administration. The results are reported in Table XII.

B) Histamine Sensitivity.

Groups of female Balb/C mice of 5-7 weeks, weighing approximately 20 g are inoculated intraperitoneally on day 0 with 0.5 ml saline apyrogen sterile physiological solution as such, or containing 0.004, 0.02, 0.04, 0.1, 0.5 and 1.0 µg PT or 2.5, 12.5, 25.0 and 50.0 µg PTF-9K/129G. At day +6 the mice were intraperitoneally inoculated with 0.5 ml apyrogen sterile saline solution containing 4 mg histamine dihydrochloride. Deaths were registered 24 hours after histamine administration. The results are reported in Table XII.

C) Leukocytosis

Groups of 5 female Balb/C mice of 5-7 weeks, weighing approximately 20 g were intraperitoneally inoculated on day 0 with 0.5 ml apyrogen sterile solution as such, or containing 0.004, 0.02, 0.04, 0.1, 0.5 and 1.0 µg PT or 2.5, 12.5, 25.0 and 50.0 µg PTF-9K/129G. On the third day after the administration, blood samples were taken from the orbital plexus of the animals and tested to determine leukocytosis. The results, expressed as average +/− the standard deviation of the leucocyte counts from 5 animals individually tested are reported in Table XII.

TABLE XII

| | Dose µg/mouse | Leucoc. (PBMC/ ml × $10^6$) | Histam. D/T[b] | Anaph. D/T[b] |
|---|---|---|---|---|
| Saline | — | 5.23 +/− 0.51 | 0/5 | 0/5 |
| PT | 0.004 | 5.94 +/− 0.41 | 0/5 | N.D. |
| | 0.020 | 10.33 +/− 0.82 | 0/5 | N.D. |
| | 0.040 | 14.34 +/− 0.83 | 0/5 | 4/5 |
| | 0.100 | 17.73 +/− 1.12 | 1/5 | 4/5 |
| | 0.500 | 45.73 +/− 3.76 | 5/5 | 5/5 |
| | 1.000 | 55.19 +/− 6.62 | 5/5 | N.D. |
| PTF-9K/129G | 2.500 | 4.45 +/− 0.41 | 0/5 | 0/5 |
| | 7.500 | N.D. | N.D. | 0/5 |
| | 12.500 | 4.39 +/− 0.32 | 0/5 | N.D. |
| | 25.000 | 4.79 +/− 0.44 | 0/5 | N.D. |
| | 50.000 | 4.71 +/− 0.35 | 0/5 | N.D. |

N.D. = not determined
[b] = equal deaths on a total of 5 mice/group

As can be seen from the Table, the intraperitoneally inoculated mice develop after three days a dose-dependent leukocytosis. The increase of the peripheral blood mononucleated cells (BPMC) is further statistically significant with 0.020 µg purified PT toxin, while the PTF-9K/129C is completely incapable of promoting leukocytosis at a dose of 50 µg/mouse. Said mutant, intraperitoneally inoculated at the same doses as above, does not induce lethal effects in the mouse following the histamine administration. PT, on the other hand, inoculated at a dose of 0.5 µg/mouse causes 100% deaths.

The capacity of the pertussis toxin to potentiate the BSA anaphylaxis, a phenomenon which was associated with the encephalopathies cause by the cellular antipertussis vaccine. is absent in as far as the PTF-9K/129G mutant is concerned. The anaphylaxis potentiation, which causes deaths in 80% of the mice inculated with 0.040 µg PT, is not observed in mice treated with 7.5 µg PTF-9K/129G.

D) Acute Toxicity

The intraperitoneal or subcutaneous study of toxicity is performed according to the directions of OMS (WHO Tech. Rep. Ser. (1979), 638: 60-80). Groups of 5 mice and 5 rats are intraperitoneally and subcutaneously inoculated with the PT-9K/129G and PTF-9K/129G mutants (1500 µg/kg of body weight). The animals were then kept under control for 14 days, during which no weight variations or other symptoms were registered which would indicate a local or systemic reaction.

EXAMPLE 9

Development of the Antipertussis Acellular Vaccine

A) Analysis of PTF-9KZ129G Mutant Immunogenicity

For the purpose of investigating the PTF-9K/129C mutant immunogenicity, groups of 6 Guinea pigs of 4 weeks age, weighing 350 g, are subcutaneously inoculated with 0.5 ml physiological apyrogen sterile saline solution containing 0.001 mg sodium-ethyl-mercurythiosalycilate and 3, 10, 25 and 50 μg PTF-9K/129C absorbed on $AL(OH)_3$ (1 mg/ml) and 0.75 ml (corresponding to 1.5 human dose) classical trivalent DPT vaccine (antidiphtheric, antipertussis and antitetanus) (SCLAVO, S.p.A.) in which the pertussis component consists of killed *B. pertussis.*

After 4 weeks from the first inoculation, blood samples are taken and the animals are subcutaneously inoculated again with the same dose of PTF-9K/129G and DPT vaccine. After 2 weeks from the second inoculation, further blood samples are taken. The sera obtained from the samples are then tested with the ELISA assay to determine the antibody and anti-PT titer and the CHO test to determine the antibodies capacity of neutralizing PT.

The ELISA assay, which is a modified version of the one described by Engvall and Perlmann (J. Immunol. 109:129-135, (1972)) is performed as follows: in each well of a polystyrene flat bottom micro plate (Dynatech laboratories Inc., Alexandria, Va.) 200 μl PBS, pH 7.4 are introduced containing 1 μg purified PT (antigen). The antigen adsorption on the solid phase is performed in a humidified chamber at 37° C. for 3 hours and then at 4° C. for one night. After minimization of the non-specific adsorption of the serum proteins on the plastic material with 1% BSA in PBS, the serum samples obtained from the Guinea pigs and serially diluted down to 1:9120 with PBS with added 0.05% Tween-20, are introduced in each micro plate well and incubated for 2 hours at 37° C. At the end, IgG goat antibodies anti-Guinea pig conjugated with alkaline phosphatase (Miles, Yeda, Israel), diluted 1:3000 in PBS 0.05% Tween-20, are introduced in each well and the plates are incubated at 37° C. for 2 hours. 100 μl volumes are utilized in all the steps and for washing the plates between incubations. The washings are carried out three times using PBS containing 0.05% Tween-20 and 0.02% $NaN_3$. The calorimetric reaction which develops at room temperature in 30 minutes after adding the specific substrate (p-nitrophenyl phosphate, 1 mg/ml) is read at 405 nm in a Titertek Multiskan (Flow Laboratories, McLean, Va.). Controls for each plate include wells with serum samples free of antigen and vice versa. The antibody titers are evaluated reporting in a graph (Abscissa) the dilutions of the serum tested in duplicate vs. the average of the respective absorbances (Ordinate). The intersection between the flex point and the absorbance axis represents the value of the undiluted serum absorbance (ABS-MAX). The ABS-MAX values obtained for each group of animals. immunized with DPT and different doses of PTF-9K/129G are compared, after each sampling, with the respective pre-immune sera (FIG. 7). The ABSMAX increase is considered statistically significant when it is at least 4 times higher than the value obtained for a pre-vaccination serum.

As can be observed from FIG. 7, the undiluted sera taken after 4 weeks after the first inoculation show absorbance values (ABS-MAX, 1 dose) at 405 nm which are from 32 to 40 times higher than the one determined before immunization. A further 50% increase is observed for the sera taken after two weeks from the second inoculation (ABSMAX, 2 doses).

The increase of the antibody titer observed after PTF-9K/129G immunization correlates with the neutralizing activity determined in the CHO test. In fact, the sera obtained after a single injection of 3, 10, 25 and 50 μg PTF-9K/129G are capable of neutralizing the agglutinating effect on CHO cells induced by 120 μg PT are the dilutions of respectively 1/20, 1/20, 1/20 and 1/80. The capacity of neutralizing the toxin increases considerably after the second immunization. In fact, antibodies obtained from animals immunized with 3 μg PTF-9K/129G are capable of neutralizing the toxin activity at a dilution of 1/1,280 (FIG. 7).

B) Analysis of the Potency of Acellular Antipertussis Vaccine in Mice

Groups of 16 CD1 (Charles River, Calco, Italy) male mice of 3-4 weeks, weighing approximately 16 g are intraperitoneally inoculated in agreement with the OMS norms with 0.5 ml sterile saline solution containing 0.24, 1.20, 1.92, 4.80, 12.00 and 30-00 μg fluid (non absorbed) PT-9K/129G and 0.24, 1.20, 6.00 and 30.00 μg of the same mutant stabilized with 0.035% formaldehyde (PTF-9K/1290) absorbed on $AL(OH)_3$ (1 mg/ml). As positive control, groups of mice are intraperitoneally inoculated with 0.00032. 0.001, 0.008 and 0.04 ml standard antipertussis cellular vaccine (National Institute of Health, Bethesda, Md.). 14 days after the administration, the mice are intracerebrally (IC) infected with a suspension of virulent D. pertussis (strain 18323; SCLAVO S.p.A.) containing 300 average lethal doses. The mice were then kept under control for 14 days.

The results are reported in Table XIII.

TABLE XIII

| Cellular[a] vaccine | | Acellular vaccine | | |
|---|---|---|---|---|
| | | PTF-9K/129G adsorbed | PT-9K/129G | |
| Dose | | dose | fluid | |
| ml | surv.[b] | μg/mouse | surv.[b] | surv.[b] |
| 0.04 | 16/16 | 30 | 14/16 | 16/16 |
| 0.008 | 13/18 | 12 | N.D.[c] | 16/16 |
| 0.0010 | 9/16 | 6 | 14/16 | N.D. |
| 0.00032 | 1/16 | 4.80 | N.D. | 12/16 |
| | | 1.92 | N.D. | 10/16 |
| | | 1.20 | 8/16 | 7/16 |
| | | 0.24 | 2/16 | 3/16 |
| | | $PD_{50}$[d] | 1.2 | 1.1 | a) the vaccine contains eight protective international units/ml;
b) the values are expressed as the number of surviving mice on a total of 16 mice tested;
c) N.D.=non determined;
d) dose which protects 50% of the mice from intracerebral infections with virulent *B. pertussis* 18323.

As can be observed from the Table, the PTF-9K/129G absorbed on $Al(OH)_3$ induces a protection from paralysis or death in 50% of mice at a dose of 1.2 μg/mouse ($PD_{50}$).

Better results are obtained with the fluid PT-9K/129G untreated with formaldehyde. In fact, each time PT-9K/129G is utilized as immunogen, 100% protection is reached immediately after IC challenge. The $PD_{50}$ (1.1 µg/mouse) does not, however, change in a significant way.

EXAMPLE 11

Clinical Experimentation of the Acellular Antipertussis Vaccine in Adult Volunteers The purpose of the study is to evaluate the tolerance and the immunogenicity (capacity of inducing specific neutralizing antibodies) of the acellular antipertussis vaccine containing PTF9K/129G as active principle in a volunteer population. For this purpose, 29 adult, healthy individuals of both sexes were selected, with anti-PT antibody titers lower than 20 ELISA units (EU)/ml. The patients are subdivided according to their anamnesis (unknown/negative for pertussis, positive for illness, positive for vaccination).

After a casual choice within each group, the patients are successively treated with:

1) antipertussis acellular vaccine containing the PTF-9K/129G mutant (18 volunteers). Each 0.5 ml dose contains 15 µg PTF-9K/129G (active principle) 0.001 mg sodium-ethyl-mercury thyosalycilate and 0.5 mg aluminum hydroxide (eccipient), or 2) placebo consisting of a aluminum hydroxide suspension, of indifferentiated aspect vis a vis the vaccine (11 volunteers). On the basis of a random choice, each patient is administered 2 doses antipertussis vaccine or 2 doses placebo, intramuscularly at the level of the left deltoid with an interval of 6 weeks between the 2 doses.

The patients are closely monitored for 3 months after the start of the experiment, and all the local and/or systemic side effects are noted. The administration of whole plasma and/or gamma human globulins in avoided starting 3 months prior to the start of the experiment and for its entire duration. In the same period of time, also the administration of cortisone compounds and/or antihypertensive drugs is avoided.

The patients are kept under strict observation for 30 minutes after the vaccine administration. Every day, for the 5 days successive to the vaccine administration, the values of the body temperature by acellular measurement are noted, and inspection and palpation of the administration site and of the satellite superficial lymphoglandular station is performed. 4 days after the antipertussis vaccine administration, a sample of peripheral venous blood is taken from each patient for the purpose of carrying out the hematological, hematochemical, immunological tests (activation markers of lymphoid cells as CD3, CD4, CD19, CD25, CD23, CD14 and CD57; in vitro proliferation with respect to the PT, PT-9K/129G and tetanus toxoid antigens). 30 days after the vaccine administration, beside the antibody titration, also the tests for the cell mediated immunity evaluation and IgE titration are performed.

The same analyses are carried out according to the methods reported above after the second vaccine or placebo administration. The absence of side effects after the first and second vaccine administration indicates a complete tolerance vs the PTF-9K/1290 mutant. For each volunteer, the antipertussis antibody titer (ELISA assay) and the neutralizing titer(CHO cells) are determined.

The results are shown in table XIV.

TABLE XIV

| Experimental group | | ELISA EU/ml | Neutralizing titer |
| --- | --- | --- | --- |
| 1) | Vaccine (pre) | 6.73 (4.64-9.77) | 13.61 (8.60-21.54) |
| 2) | Vaccine (post) | 496.54 (199.91-1233.35) | 1810.19 (737.02-4446.01) |
| 3) | Vaccine (post/pre) | 73.76 | 133.02 |
| 4) | Placebo (pre) | 6.51 (3.67-11.54) | 12.87 (7.07-23.42) |
| 5) | Placebo (post) | 8.09 (4.67-14.62) | 12.87 (7.07-23.42) |
| 6) | Placebo (post/pre) | 1.24 | 1.00 |

The anti-PT-antibody titer is expressed as geometric average of a standard reference serum (US Reference Human Pertussis Antiserum. Lot n. 3, FDA, Bethesda, U.S.A. kindly supplied by Dr. J. Manclark), while the neutralizing titer is expressed as the maximum serum dilution capable of inhibition the agglutinating effect of the native toxin on CHO cells. The values in parenthesis represent the fiducial 95% limits determined with students "t" test.

In the preceding Table, the increment (post/pre) of the antibody titer and of the neutralizing one determined before (pre) and after administration of vaccine and of placebo is reported.

What is claimed is:

1. *Bordetella pertussis, Bordetella parapertussis,* or *Bordetella bronchiseptica* strains characterized in that they contain in their chromosome the gene coding for pertussis toxin (PT) and its expression and secretion regulation sequences wherein the nucleotide sequence of the S1 subunit of said gene is mutagenized so as to code for a pertussis toxin of no or reduced toxicity by having said nucleotide sequence coding for the amino acid Glu at PT position 129 changed to a sequence coding for the amino acid Gly, and by having a further change selected from the group consisting of: (1) said sequence coding for the amino acid Arg at PT position 9 changed to a sequence coding for Lys, (2) said sequence coding for the amino acid Arg at PT position 13 changed to a sequence coding for Leu, and (3) said sequence coding for the amino acid Trp at PT position 26 changed to a sequence coding for Ile.

2. A strain of *Bordetella pertussis* having its chromosomal gene coding for pertussis toxin (PT) replaced by a chromosomal gene coding for PT wherein the nucleotide sequence for the S1 subunit thereof is mutagenized by having said sequence coding for the amino acid Glu at PT position 129 changed to a sequence coding for the amino acid Gly, and by having a further change selected from the group consisting of: (1) said sequence coding for the amino acid Arg at PT position 9 changed to a sequence coding for Lys, (2) said sequence coding for the amino acid Arg at PT position 13 changed to a sequence coding for Leu, and (3) said sequence coding for the amino acid Trp at PT position 26 changed to a sequence coding for Ile.

3. The strain of *Bordetella pertussis* of claim 2 wherein said further change is said sequence coding for the amino acid Arg at PT position 9 changed to a sequence coding for Lys.

4. The strain of *Bordetella pertussis* of claim 2 wherein said further change is said sequence coding for the amino acid Arg at PT position 13 changed to a sequence coding for Leu.

5. The strain of *Bordetella pertussis* of claim 2 wherein said further change is said sequence coding for the amino acid Trp at PT position 26 changed to a sequence coding for Ile.

6. A mutated chromosomal gene coding for pertussis toxin (PT) wherein the nucleotide sequence for the S1 subunit of said gene is mutagenized by having said sequence coding for the amino acid Glu at PT position 129 changed to a sequence coding for the amino acid Gly, and by having a further change selected from the group consisting of: (1) said sequence coding for the amino acid Arg at PT position 9 changed to a sequence coding for Lys, (2) said sequence coding for the amino acid Arg at PT position 13 changed to a sequence coding for Leu, and (3) said sequence coding for the amino acid Trp at PT position 26 changed to a sequence coding for Ile.

7. The chromosomal gene of claim 6 wherein said further change is said sequence coding for the amino acid Arg at PT position 9 changed to a sequence coding for Lys.

8. The chromosomal gene of claim 6 wherein said further change is said sequence coding for the amino acid Arg at PT position 13 changed to a sequence coding for Leu.

9. The chromosomal gene of claim 6 wherein said further change is said sequence coding for the amino acid Trp at PT position 26 changed to a sequence coding for Ile.

* * * * *